US 9,486,285 B2

United States Patent
Paithankar et al.

(10) Patent No.: US 9,486,285 B2
(45) Date of Patent: Nov. 8, 2016

(54) TREATMENT OF SKIN BY SPATIAL MODULATION OF THERMAL HEATING

(75) Inventors: Dilip Y. Paithankar, Natick, MA (US); Jayant D. Bhawalkar, Brighton, MA (US); James C. Hsia, Weston, MA (US)

(73) Assignee: CANDELA CORPORATION, Wayland, MA (US)

( * ) Notice: Subject to any disclaimer, the term of this patent is extended or adjusted under 35 U.S.C. 154(b) by 1078 days.

(21) Appl. No.: 13/584,440

(22) Filed: Aug. 13, 2012

(65) Prior Publication Data

US 2012/0310235 A1 Dec. 6, 2012

Related U.S. Application Data

(62) Division of application No. 11/763,111, filed on Jun. 14, 2007, now Pat. No. 8,246,611.

(60) Provisional application No. 60/813,729, filed on Jun. 14, 2006.

(51) Int. Cl.
*A61B 18/18* (2006.01)
*A61B 18/20* (2006.01)
*A61B 18/00* (2006.01)

(52) U.S. Cl.
CPC .... *A61B 18/203* (2013.01); *A61B 2018/00005* (2013.01); *A61B 2018/00029* (2013.01); *A61B 2018/00452* (2013.01); *A61B 2018/00458* (2013.01); *A61B 2018/208* (2013.01)

(58) Field of Classification Search
CPC .................. A61B 18/203; A61B 2018/00452; A61B 2018/00458; A61B 2018/203
See application file for complete search history.

(56) References Cited

U.S. PATENT DOCUMENTS

| 3,404,350 A | 10/1968 | Muncheryan |
| 3,538,919 A | 11/1970 | Meyer et al. |
| 3,693,623 A | 9/1972 | Harte et al. |

(Continued)

FOREIGN PATENT DOCUMENTS

| AU | 60343/90 | 6/1992 |
| CA | 1041610 | 10/1978 |

(Continued)

OTHER PUBLICATIONS

Alster, T., "Laser Hair Removal: Are the Results Permanent?," *Laser Focus*, 21-23 (1993).

(Continued)

*Primary Examiner* — Kaitlyn Smith
(74) *Attorney, Agent, or Firm* — Manelli Selter PLLC; Edward J. Stemberger

(57) ABSTRACT

Treating skin can include delivering a beam of radiation to a target region of the skin to cause a zone of thermal injury including a lateral pattern of varying depths of thermal injury distributed along the target region. The lateral pattern includes at least one first sub-zone of a first depth of thermal injury laterally adjacent to at least one second sub-zone of a second depth of thermal injury. The first depth is greater than the second depth. The at least one first sub-zone of the first depth and the at least one second sub-zone of the second depth extend from a surface of the target region of the skin to form a substantially continuous surface thermal injury. The at least one first sub-zone of the first depth and the at least one second sub-zone of the second depth are substantially heated to at least a critical temperature.

14 Claims, 13 Drawing Sheets

(56) References Cited

U.S. PATENT DOCUMENTS

| | | |
|---|---|---|
| 3,769,963 A | 11/1973 | Goldman et al. |
| 3,834,391 A | 9/1974 | Block |
| 3,900,034 A | 8/1975 | Katz et al. |
| 3,916,143 A | 10/1975 | Farrell |
| 4,388,924 A | 6/1983 | Weissman et al. |
| 4,461,294 A | 7/1984 | Baron |
| 4,608,978 A | 9/1986 | Rohr |
| 4,617,926 A | 10/1986 | Sutton |
| 4,672,969 A | 6/1987 | Dew |
| 4,733,660 A | 3/1988 | Itzkan |
| 4,819,669 A | 4/1989 | Politzer |
| 4,854,320 A | 8/1989 | Dew et al. |
| 4,874,361 A | 10/1989 | Obagi |
| 4,917,084 A | 4/1990 | Sinofsky |
| 4,930,504 A | 6/1990 | Diamantopoulos et al. |
| 4,976,709 A | 12/1990 | Sand |
| 5,000,752 A | 3/1991 | Hoskin et al. |
| 5,002,051 A | 3/1991 | Dew et al. |
| 5,019,034 A | 5/1991 | Weaver et al. |
| 5,057,104 A | 10/1991 | Chess |
| 5,059,192 A | 10/1991 | Zaias |
| 5,133,708 A | 7/1992 | Smith |
| 5,137,530 A | 8/1992 | Sand |
| 5,139,495 A | 8/1992 | Daikuzono |
| 5,140,984 A | 8/1992 | Dew et al. |
| 5,151,098 A | 9/1992 | Loertscher |
| 5,182,857 A | 2/1993 | Simon |
| 5,226,907 A | 7/1993 | Tankovich |
| 5,282,797 A | 2/1994 | Chess |
| 5,290,273 A | 3/1994 | Tan |
| 5,304,169 A | 4/1994 | Sand |
| 5,304,170 A | 4/1994 | Green |
| 5,312,395 A | 5/1994 | Tan et al. |
| 5,320,618 A | 6/1994 | Gustafsson |
| 5,334,190 A | 8/1994 | Seiler |
| 5,336,217 A | 8/1994 | Buys et al. |
| 5,344,418 A | 9/1994 | Ghaffari |
| 5,348,551 A | 9/1994 | Spears et al. |
| 5,360,425 A | 11/1994 | Cho |
| 5,374,265 A | 12/1994 | Sand |
| 5,397,327 A | 3/1995 | Koop et al. |
| 5,405,368 A | 4/1995 | Eckhouse |
| 5,409,479 A | 4/1995 | Dew et al. |
| 5,423,803 A | 6/1995 | Tankovich et al. |
| 5,425,728 A | 6/1995 | Tankovich |
| 5,437,658 A | 8/1995 | Muller et al. |
| 5,445,146 A | 8/1995 | Bellinger |
| 5,445,634 A | 8/1995 | Keller |
| 5,464,436 A | 11/1995 | Smith |
| 5,474,549 A | 12/1995 | Ortiz et al. |
| 5,484,432 A | 1/1996 | Sand |
| 5,486,172 A | 1/1996 | Chess |
| 5,522,813 A | 6/1996 | Trelles |
| 5,527,350 A | 6/1996 | Grove et al. |
| 5,549,660 A | 8/1996 | Mendes et al. |
| 5,558,667 A | 9/1996 | Yarborough et al. |
| 5,569,242 A | 10/1996 | Lax et al. |
| 5,569,663 A | 10/1996 | Ribier et al. |
| 5,591,157 A | 1/1997 | Hennings et al. |
| 5,606,798 A | 3/1997 | Kelman |
| 5,618,284 A | 4/1997 | Sand |
| 5,620,478 A | 4/1997 | Eckhouse |
| 5,626,631 A | 5/1997 | Eckhouse |
| 5,643,334 A | 7/1997 | Eckhouse et al. |
| 5,647,866 A | 7/1997 | Zaias et al. |
| 5,653,706 A | 8/1997 | Zavislan et al. |
| 5,660,836 A | 8/1997 | Knowlton |
| 5,679,691 A | 10/1997 | Ribier et al. |
| 5,683,380 A | 11/1997 | Eckhouse et al. |
| 5,707,403 A | 1/1998 | Grove et al. |
| 5,713,845 A | 2/1998 | Tankovich |
| 5,720,772 A | 2/1998 | Eckhouse |
| 5,735,844 A | 4/1998 | Anderson et al. |
| 5,746,736 A | 5/1998 | Tankovich |
| 5,749,868 A | 5/1998 | Furumoto |
| 5,752,948 A | 5/1998 | Tankovich et al. |
| 5,752,949 A | 5/1998 | Tankovich et al. |
| 5,754,573 A | 5/1998 | Yarborough et al. |
| 5,755,753 A | 5/1998 | Knowlton |
| 5,760,407 A | 6/1998 | Margosiak et al. |
| 5,800,479 A | 9/1998 | Thiberg |
| 5,810,801 A | 9/1998 | Anderson et al. |
| 5,814,040 A | 9/1998 | Nelson et al. |
| 5,817,089 A | 10/1998 | Tankovich et al. |
| 5,817,090 A | 10/1998 | Abergel et al. |
| 5,820,626 A | 10/1998 | Baumgardner |
| 5,836,999 A | 11/1998 | Eckhouse et al. |
| 5,843,072 A | 12/1998 | Furumoto et al. |
| 5,860,967 A | 1/1999 | Zavislan et al. |
| 5,868,732 A | 2/1999 | Waldman et al. |
| 5,871,479 A | 2/1999 | Furumoto et al. |
| 5,871,480 A | 2/1999 | Tankovich |
| 5,871,524 A | 2/1999 | Knowlton |
| 5,880,292 A | 3/1999 | DeLuca et al. |
| 5,897,549 A | 4/1999 | Tankovich |
| 5,919,219 A | 7/1999 | Knowlton |
| 5,925,035 A | 7/1999 | Tankovich |
| 5,948,011 A | 9/1999 | Knowlton |
| 5,964,749 A | 10/1999 | Eckhouse et al. |
| 5,979,454 A | 11/1999 | Anvari et al. |
| 5,984,915 A | 11/1999 | Loeb et al. |
| 5,997,530 A | 12/1999 | Nelson et al. |
| 6,030,378 A | 2/2000 | Stewart |
| 6,036,684 A | 3/2000 | Tankovich et al. |
| 6,045,548 A | 4/2000 | Furumoto et al. |
| 6,050,990 A | 4/2000 | Tankovich et al. |
| 6,059,820 A | 5/2000 | Baronov |
| 6,063,074 A | 5/2000 | Tankovich |
| 6,063,108 A | 5/2000 | Salansky et al. |
| 6,077,294 A | 6/2000 | Cho et al. |
| 6,083,217 A | 7/2000 | Tankovich |
| 6,096,029 A | 8/2000 | O'Donnell, Jr. |
| 6,106,514 A | 8/2000 | O'Donnell, Jr. |
| 6,120,497 A | 9/2000 | Anderson et al. |
| 6,135,994 A | 10/2000 | Chernoff |
| 6,148,232 A | 11/2000 | Avrahami |
| 6,149,645 A * | 11/2000 | Tobinick ............... A61B 18/203 606/10 |
| 6,152,917 A | 11/2000 | Tankovich |
| 6,162,211 A | 12/2000 | Tankovich et al. |
| 6,165,171 A * | 12/2000 | Tobinick ............... A61B 18/203 606/11 |
| 6,168,590 B1 | 1/2001 | Neev |
| 6,176,854 B1 | 1/2001 | Cone |
| 6,183,773 B1 | 2/2001 | Anderson |
| 6,200,308 B1 * | 3/2001 | Pope .................... A61B 18/203 606/11 |
| 6,217,572 B1 * | 4/2001 | Tobinick ................ A61B 18/22 606/10 |
| 6,228,075 B1 | 5/2001 | Furumoto |
| 6,235,016 B1 | 5/2001 | Stewart |
| 6,241,753 B1 | 6/2001 | Knowlton |
| 6,267,771 B1 | 7/2001 | Tankovich et al. |
| 6,273,883 B1 | 8/2001 | Furumoto |
| 6,280,438 B1 | 8/2001 | Eckhouse et al. |
| 6,283,956 B1 | 9/2001 | McDaniel |
| 6,306,130 B1 | 10/2001 | Anderson et al. |
| 6,311,090 B1 | 10/2001 | Knowlton |
| 6,350,276 B1 | 2/2002 | Knowlton |
| 6,377,854 B1 | 4/2002 | Knowlton |
| 6,377,855 B1 | 4/2002 | Knowlton |
| 6,381,497 B1 | 4/2002 | Knowlton |
| 6,381,498 B1 | 4/2002 | Knowlton |
| 6,387,089 B1 | 5/2002 | Kreindel et al. |
| 6,387,380 B1 | 5/2002 | Knowlton |
| 6,402,739 B1 | 6/2002 | Neev |
| 6,405,090 B1 | 6/2002 | Knowlton |
| 6,406,474 B1 | 6/2002 | Neuberger et al. |
| 6,413,255 B1 | 7/2002 | Stern |
| 6,425,912 B1 | 7/2002 | Knowlton |
| 6,427,089 B1 | 7/2002 | Knowlton |
| 6,430,446 B1 | 8/2002 | Knowlton |
| 6,438,424 B1 | 8/2002 | Knowlton |
| 6,453,202 B1 | 9/2002 | Knowlton |

(56) References Cited

U.S. PATENT DOCUMENTS

| | | |
|---|---|---|
| 6,461,378 B1 | 10/2002 | Knowlton |
| 6,470,216 B1 | 10/2002 | Knowlton |
| 6,508,813 B1* | 1/2003 | Altshuler ............ A61B 18/203 606/16 |
| 6,569,156 B1 | 5/2003 | Tankovich et al. |
| 6,597,946 B2 | 7/2003 | Avrahami et al. |
| 6,605,080 B1 | 8/2003 | Altshuler et al. |
| 6,610,052 B2 | 8/2003 | Furumoto |
| 6,611,706 B2 | 8/2003 | Avrahami et al. |
| 6,613,040 B2 | 9/2003 | Tankovich et al. |
| 6,613,042 B1 | 9/2003 | Tankovich et al. |
| 6,615,079 B1 | 9/2003 | Avrahami |
| 6,632,219 B1 | 10/2003 | Baranov et al. |
| 6,659,999 B1 | 12/2003 | Anderson et al. |
| 6,708,060 B1 | 3/2004 | Avrahami et al. |
| 6,711,435 B2 | 3/2004 | Avrahami et al. |
| 6,723,090 B2 | 4/2004 | Altshuler et al. |
| 6,743,222 B2 | 6/2004 | Durkin et al. |
| 6,749,624 B2 | 6/2004 | Knowlton |
| 6,997,923 B2 | 2/2006 | Anderson et al. |
| 7,006,874 B2 | 2/2006 | Knowlton et al. |
| 7,022,121 B2 | 4/2006 | Stern et al. |
| 7,041,094 B2 | 5/2006 | Connors et al. |
| 7,115,123 B2 | 10/2006 | Knowlton et al. |
| 7,118,562 B2 | 10/2006 | Furumoto |
| 7,141,049 B2 | 11/2006 | Stern et al. |
| 7,189,230 B2 | 3/2007 | Knowlton |
| 7,780,656 B2 | 8/2010 | Tankovich |
| 7,814,915 B2 | 10/2010 | Davenport et al. |
| 2002/0062142 A1 | 5/2002 | Knowlong |
| 2002/0099094 A1 | 7/2002 | Anderson |
| 2002/0161357 A1 | 10/2002 | Anderson et al. |
| 2002/0169442 A1 | 11/2002 | Neev |
| 2002/0173833 A1 | 11/2002 | Korman et al. |
| 2002/0183724 A1 | 12/2002 | Neev |
| 2002/0183789 A1 | 12/2002 | Neev |
| 2003/0004501 A1 | 1/2003 | Wilkens et al. |
| 2003/0032900 A1* | 2/2003 | Ella ..................... A61H 7/008 601/6 |
| 2003/0032950 A1* | 2/2003 | Altshuler ............ A61B 17/545 606/9 |
| 2003/0036749 A1 | 2/2003 | Durkin et al. |
| 2003/0216719 A1 | 11/2003 | Debenedictis et al. |
| 2003/0220635 A1 | 11/2003 | Knowlton et al. |
| 2004/0002704 A1 | 1/2004 | Knowlton et al. |
| 2004/0087889 A1* | 5/2004 | Simonsen ............ A61B 18/203 604/20 |
| 2004/0127815 A1 | 7/2004 | Marchitto et al. |
| 2004/0143247 A1 | 7/2004 | Anderson et al. |
| 2005/0049582 A1 | 3/2005 | DeBenedictis et al. |
| 2005/0059940 A1* | 3/2005 | Weber ................. A61M 37/00 604/289 |
| 2005/0222555 A1 | 10/2005 | Manstein et al. |
| 2005/0222565 A1 | 10/2005 | Manstein |
| 2005/0256515 A1 | 11/2005 | Anderson et al. |
| 2006/0004306 A1* | 1/2006 | Altshuler ............ A61B 18/203 601/3 |
| 2006/0025837 A1 | 2/2006 | Stern et al. |
| 2006/0058712 A1 | 3/2006 | Altshuler et al. |
| 2006/0122585 A1 | 6/2006 | Connors et al. |
| 2006/0122668 A1 | 6/2006 | Anderson et al. |
| 2006/0155266 A1 | 7/2006 | Manstein et al. |
| 2006/0206110 A1 | 9/2006 | Knowlton et al. |
| 2006/0247609 A1 | 11/2006 | Mirkov et al. |
| 2007/0010811 A1 | 1/2007 | Stern et al. |
| 2007/0027440 A1 | 2/2007 | Altshuler et al. |
| 2007/0038206 A1* | 2/2007 | Altshuler ............ A46B 15/0036 606/20 |
| 2007/0073367 A1 | 3/2007 | Jones et al. |
| 2007/0118098 A1 | 5/2007 | Tankovich |
| 2007/0129711 A1* | 6/2007 | Altshuler ............ A45D 26/0061 606/9 |
| 2007/0219540 A1 | 9/2007 | Masotti et al. |
| 2007/0239147 A1 | 10/2007 | Manstein et al. |
| 2007/0255355 A1 | 11/2007 | Altshuler et al. |
| 2008/0009842 A1 | 1/2008 | Manstein et al. |
| 2008/0015555 A1 | 1/2008 | Manstein et al. |
| 2008/0021442 A1 | 1/2008 | Manstein et al. |
| 2008/0139901 A1 | 6/2008 | Altshuler et al. |
| 2008/0161888 A1 | 7/2008 | Hsia |
| 2008/0188847 A1 | 8/2008 | Gustavsson |
| 2008/0188914 A1 | 8/2008 | Gustavsson |
| 2008/0200908 A1 | 8/2008 | Domankevitz |
| 2008/0215040 A1 | 9/2008 | Paithankar et al. |
| 2008/0262482 A1 | 10/2008 | Hantash et al. |
| 2008/0294150 A1 | 11/2008 | Altshuler et al. |
| 2008/0294152 A1* | 11/2008 | Altshuler .................. G01P 3/36 606/9 |
| 2009/0131922 A1 | 5/2009 | Dewey et al. |
| 2009/0254076 A1 | 10/2009 | Altshuler et al. |
| 2010/0022922 A1 | 1/2010 | Barthe et al. |
| 2010/0036295 A1 | 2/2010 | Altshuler et al. |
| 2010/0168824 A1 | 7/2010 | Toriser |
| 2011/0015625 A1 | 1/2011 | Adanny et al. |
| 2011/0130618 A1* | 6/2011 | Ron Edoute ............ A61N 1/328 600/14 |
| 2011/0218464 A1 | 9/2011 | Iger |
| 2011/0251602 A1 | 10/2011 | Anderson et al. |
| 2011/0295187 A1* | 12/2011 | Shanks ..................... C02F 1/325 604/20 |

FOREIGN PATENT DOCUMENTS

| | | |
|---|---|---|
| CA | 2131750 | 1/1996 |
| DE | 195 12 481 | 10/1995 |
| DE | 198 32 221 | 7/2000 |
| EP | 0 142 671 | 5/1985 |
| EP | 0 292 621 | 11/1988 |
| EP | 0 348 862 | 1/1990 |
| EP | 0 575 274 | 12/1993 |
| EP | 0 724 866 | 8/1996 |
| EP | 0 724 894 | 8/1996 |
| EP | 0763371 A2 | 3/1997 |
| EP | 0 933 096 | 8/1999 |
| EP | 1 147 785 | 10/2001 |
| GB | 2 123 287 | 2/1984 |
| JP | 63-249577 | 10/1988 |
| JP | 64-080309 | 3/1989 |
| JP | 03-193003 | 8/1991 |
| JP | 04-067860 | 3/1992 |
| JP | 04-322668 | 11/1992 |
| JP | 5-329218 | 12/1993 |
| WO | WO 84/02644 | 7/1984 |
| WO | WO 86/02783 | 5/1986 |
| WO | WO 89/00027 | 1/1989 |
| WO | WO 91/01727 | 2/1991 |
| WO | WO 91/13653 | 9/1991 |
| WO | WO 92/16338 | 10/1992 |
| WO | WO 92/19165 | 11/1992 |
| WO | WO 93/05920 | 4/1993 |
| WO | WO 95/15134 | 6/1995 |
| WO | WO 95/15725 | 6/1995 |
| WO | WO 96/23447 | 8/1996 |
| WO | WO 97/37723 | 10/1997 |
| WO | WO 99/07438 | 2/1999 |
| WO | WO 99/27863 | 6/1999 |
| WO | WO 99/34867 | 7/1999 |
| WO | WO 99/49937 | 10/1999 |
| WO | WO 00/02491 | 1/2000 |
| WO | WO 00/09023 | 2/2000 |
| WO | WO 00/32272 | 6/2000 |
| WO | WO 00/64537 | 11/2000 |
| WO | WO 02/053050 | 7/2002 |
| WO | WO 2005/096980 | 10/2005 |

OTHER PUBLICATIONS

Anderson et al., "The Optics of Human Skin," *The Journal of Investigative Dermatology*, 77(1):13-19 (1981).

Anderson et al., "Lasers in Dermatology Provide a Model for Exploring New Applications in Surgical Oncology," *International Advances in Surgical Oncology*, 5:341-358 (1982).

(56) References Cited

OTHER PUBLICATIONS

Anderson et al., "Selective Photothermolysis: Precise Microsurgery by Selective Absorption of Pulsed Radiation," *Science*, 220:524-527 (1983).

Anderson, R., "Optics of the Skin," in *Clinical Photomedicine*, ed. Marcel Dekker Inc., New York, New York, 28-31 (1993).

Anvari et al., "Dynamic Epidermal Cooling in Conjunction with Laser Treatment of Port-Wine Stains: Theoretical and Preliminary Clinical Evaluations," *Lasers in Medical Science*, 10:105-112 (1995).

Anvari et al., "D1 Evaluations," *Lasers in Medical Science*, 10:105-112 (1995).

Anvari et al., "A Theoretical Study of the Thermal Response of Skin Cryogen Spray Cooling and Pulsed Laser Irradiation: Implications for Treatment of Port Wine Stain Birthmarks," *Phys. Med. Biol.*, 40:1451-1465 (1995).

Anvari et al., "Selective Cooling of Biological Tissues: Application for Thermally Mediated Therapeutic Procedures," *Phys. Med. Biol.*, 40:241-252 (1995).

Anvari et al., "Selective Cooling of Biological Tissues During Pulsed Laser Irradiation," Abstract 17, *American Society for Laser Medicine and Surgery*, Abstracts (1995).

Awan, K., "Argon Laser Treatment of Trichiasis," *Ophthalmic Surgery*, 17(10):658-660 (1986).

Bartley et al., "An Experimental Study to Compare Methods of Eyelash Ablation," *Ophthalmology*, 94:1286-1289 (1987).

Berlien et al., "Lasers in Pediatric Surgery," *Progress in Pediatric Surgery*, 25:5-22 (1990).

Blankenhorn, "The Infiltration of Cartenoids Into Human Atheromas and Xanthomas," *Annals of Internal Medicine*, 53(5):944-954 (1960).

Campbell, D.C., "Thermoablation Treatment for Trichiasis Using the Argon Laser," *Australian and New Zealand Journal of Ophthalmology*, 18(4):427-430 (1990).

Ceburkov et al., "Photodynamic Therapy in Dermatology," *Eur. J. Dermatol.*, 10:568-575 (2000).

Choi et al., "Acne Fulminans and 13-Cis-Retinoic Acid," *The Journal of Dermatology*, 19(6):378-383 (1992).

Dixon et al., "Argon and Neodymium YAG Laser Therapy of Dark Nodular Port Wine Stains in Older Patients," *Lasers in Surgery and Medicine*, 6:5-11 (1986).

David et al., "Laser Abrasion for Cosmetic and Medical Treatment of Facial Actinic Damage," *CUITS*, 43(6):583-587 (1989).

Dover et al., "Pigmented Guinea Pig Skin Irradiated With Q-Switched Ruby Laser Pulses," *Arch. Dermatol.*, 125:43-49 (1989).

Dover et al., "Illustrated Cutaneous Laser Surgery," in *A Practioner's Guide*, ed. Appleton & Lange, Norwalk, Connecticut (1990).

Dover et al., "Laser Skin Resurfacing," *Seminars in Cutaneous Medicine and Surgery*, 15(3):177-188 (1996).

Eckes et al., "Collagens and the Reestablishment of Thermal Integrity," in *The Molecular and Cellular Biology of Wound Repair*, ed. Clark, R., Plenum Press, New York, New York, Chapter 16, 493-512 (1996).

Elsner, "Sebum," in *Bioengineering of the Skin: Methods and Instrumentation*, eds. CRC Press Boca Raton, FL, pp. 81-89 (1995).

Finkel et al., "Pulsed Alexandrite Laser Technology for Noninvasive Hair Removal," *Journal of Clinical Laser Medicine & Surgery*, 15 (5):225-229 (1997).

Finkelstein et al., "Epilation of Hair-Bearing Urethral Grafts Using the Neodymium:YAG Surgical Laser," *The Journal of Urology*, 146:840-842 (1991).

Fitzpatrick et al., "Pulsed Carbon Dioxide Laser Resurfacing of Photaged Facial Skin," *Arch. Dermatol.*, 132:395-402 (1996).

Fournier et al., "Nonablative Remodeling: A 14-Month Clinical Ultrasound Imaging and Profilometric Evaluation of a 1540 nm Er:Glass Laser," *Dermatol Surg*, 28:926-931 (2002).

Gilchrest et al., "Chilling Port Wine Stains Improves the Response to Argon Laser Therapy," *Plastic and Reconstructive Surgery*, 69(2):278-283 (1982).

Goldman et al., "Effect of the Laser Beam on the Skin: Preliminary Report," *The Journal of Investigative Dermatology*, 40:121-122 (1963).

Goldman et al., "Effect of the Laser Beam on the Skin: III. Exposure of Cytological Preparations," *The Journal of Investigative Dermatology*, 247-251 (1963).

Goldman et al., "Pathology of the Effect of the Laser Beam on the Skin," *Nature*, 197(4870):912-914 (1963).

Goldman et al., "The Biomedical Aspects of Lasers," *JAMA*, 188(3):230-234(1964).

Goldman et al., "Impact of the Laser on Nevi and Melanomas," *Archives of Dermatology*, 90:71-75(1964).

Goldman et al., "The Effect of Repeated Exposures to Laser Beams," *Acta Dermato-Venerologica*, 44:264-268 (1964).

Goldman et al., "Radiation From a Q-Switched Ruby Laser," *The Journal of Investigative Dermatology*, 69-71 (1964).

Goldman et al., "Treatment of Basal Cell Epithelioma by Laser Radiation," *JAMA*, 180(10):773-775 (1964).

Goldman, L., "Dermatologic Manifestations of Laser Radiation," Proceedings of the First Annual Conference on Biologic Effects of Laser Radiation, Federation of American Societies for Experimental Biology, Supp. No. 14:S-92-S-93 (Jan.-Feb. 1965).

Goldman, L., "Comparison of the Biomedical Effects of the Exposure to Low and High Energy Lasers," *Annals of New York Academy of Sciences*, 802-831 (1965).

Goldman et al., "Laser Action at the Cellular Level," *JAMA*, 198(6):641-644 (1966).

Goldman et al., "Investigative Studies With Quartz Rods for High Energy Laser Transmission," *Medical Research Engineering*, 12-17 (1967).

Goldman et al., "Laser Treatment of Tattoos," *JAMA*, 201(11):841-844 (1967).

Goldman et al., "Replica Microscopy and Scanning Electron Microscopy of Laser Impacts on the Skin," *The Journal of Investigative Dermatology*, 32(1):18-24 (1968).

Goldman et al., "Investigative Studies with the Laser in the Treatment from Basal Cell Epitheliomas," *Southern Medical Journal*, 61:735-742 (1968).

Goldman, L., "The Skin," *Arch. Environ. Health*, 18:434-436 (1969).

Goldman et al., "Preliminary Investigation of Fat Embolization for Pulsed Ruby Laser Impacts of Bone," *Nature*, 221:361-363 (1969).

Goldman et al., "Long-Term Laser Exposure of a Senile Freckle," *Arch. Environ Health*, 22:401-403 (1971).

Goldman et al., "The Laser in Dermatology," in *Lasers in Medicine*, ed: Gordon and Breach, New York, New York, 329-352 (1971).

Goldman, L., "Effects of New Laser Systems on the Skin," *Arch. Dermatol.*, 108:385-390 (1973).

Goldman, L., "Laser Surgery for Skin Cancer," *New York State Journal of Medicine*, 1897-1900 (1977).

Goldman, L., "Surgery by Laser for Malignant Melanoma," *J. Dermatol. Surg. Oncol.*, 5(2):141-144 (1979).

Gossman et al., "Experimental Comparison of Laser and Cryosurgical Cilia Destruction," *Ophthalmic Surgery*, 23(3):179-182 (1992).

Gossman et al., "Prospective Evaluation of the Argon Laser in the Treatment of Tichiasis," *Ophthalmic Surgery*, 23(3):183-187 (1992).

Greenberg et al., "A Clinical Trial of Beta-Carotene to Prevent Basal Cell and Squamous Cell Cancers of the Skin," *New England Journal of Medicine*, 323(12):789-795 (1990).

Grossman et al., "Damage to Hair Follicles by Normal-Mode Ruby Laser Pulses," *Journal of the American Academy of Dermatology*, 35:889-894 (1996).

http://www.quantel-medical.fr/US/produits/ficheProduit.php?idProd=20, last viewed Dec. 18, 2003.

Haina et al., "Possibilities for the Increase of the Coagulation Depth in Skin with the Argonlaser," in *Waidelich W*, eds. Springer, Berlin—Heidelberg—New York—Tokyo (1987).

(56) References Cited

OTHER PUBLICATIONS

Haina et al., "Improvement of Therapy Results in Treatment of Port Wine Stains with the Argonlaser," in *Waidelich W,* eds. Springer, Berlin—Heidelberg—New York—Tokyo (1987).
Hale et al., "Optical Constants of Water in the 200 nm to 200 μm Wavelength Region," *Appl. Opt.,* 12:555-563, (1973).
Hellwig et al., "Treatment of Vascular Malformations and Benign Pigmented Lesions by Pulsed Dye Laser, Photoderm VL, and Q-Switched Ruby Laser,"(Abstract) *Laryngo-Rhino-Otol.,* 74:634-641 (1995).
Hongcharu et al., "Topical ALA-Photodynamic Therapy for the Treatment of Acne Vulgaris," *Journal of Investigative Dermatology,* 115:183-192 (2000).
Hosokawa et al., "Treatment of Large Xanthomas by the Use of Blepharoplasty Island Musculocutaneous Flaps," *Annals of Plastic Surgery,* 18(3):238-240 (1987).
Huerter et al., "Multiple Eruptive Vellus Hair Cysts Treated with Carbon Dioxide Laser Vaporization," *Journ. Dermatol. Surg. Oncol.,* 13(3):260-263 (1987).
Hunt et al., "A Comparative Study of Gluconolactone Versus Benzoyl Peroxide in the Treatment of Acne," *The Australasian Journal of Dermatology,* 33(3): 131-134 (1992).
Ito et al., "Sebaceous Gland Hyperplasia on Rabbit Pinna Induced by Tetradecane," *The Journal of Investigative Dermatology,* 85(3):249-254 (1985).
Ito et al., "Photodynamic Therapy of Acne Vulgaris With Topical δ-Aminolaevulinic Acid and Incoherent Light in Japanese Patients," *British Journal of Dermatology,* 144:575-579 (2001).
Iwasaki et al., "Development of Laser Systems for Treatment of Hyperpigmented Skin Lesions," *Japanese Journal of Medical Electronics and Biological Engineering,* 27:26-34 (1989).
Kalka et al., "Photodynamic Therapy in Dermatology," *J. Am. Acad. Dermatol.,* 42:389-413 (2000).
Karrer et al., "Long-pulse Dye Laser for Photodynamic Therapy: Investigations In Vitro and In Vivo," *Lasers Surg., Med.* 25:51-59 (1999).
Kincade, K., "First Laser Hair-Removal System Gains FDA Clearance," *Laser Focus World,* Jun. 1995.
Kincade, K., "New Procedures Push Tissue Studies Beneath the Surface," *Laser Focus World,* August, 57-63 (1995).
Kincade, K., "Wrinkles Shrivel Under Fire From Pulsed Lasers," *New Scientist,* 1984:25 (Jul. 1995).
Klein et al., "Biological Effects of Laser Radiation I: Threshold Studies and Reversible Depigmentation in Rodent Skin," *Nerem Record,* 108-109 (1965).
Kuhns et al., "Biological Effects of Laser Radiation II: Effects of Laser Irradiation on the Skin," *Nerem Record* (1965).
Kuhns et al., "Laser Injury in Skin," *Laboratory Investigation,* 17(1):1-13 (1967).
Kuligowski et ., "Xanthoma Disseminatum," *International Journal of Dermatology,* 31(4):281-283 (1992).
Kuriloff, et al., "Pharyngoesophageal Hair Growth: The Role of Laser Epilation," *Case Reports,* 98(4):342-345 (1988).
Landthaler et al., "Neodymium-YAG Laser Therapy for Vascular Lesions," *Journal of the American Academy of Dermatology,* 14(1):107-117 (1986).
Laor et al., "The Pathology of Laser Irradiation of the Skin and Body Wall of the Mouse," *Laser Irradiation,* 47(4):643663 (1965).
Lask et al., "Neodymium:Yttrium-Aluminum-Garnet Laser for the Treatment of Cutaneous Lesions," *Clinics in Dermatology,* 13:81-86 (1995).
Levy et al., "Determination of Optimal Parameters for Laser for Nonablative Remodeling with a 1.54 μm Er:Glass Laser: A Dose-Response Study," *Dermatol. Surg.,* 28:405-409 (2002).
Leyden, "New Understanding of the Pathogenesis of Acne," *The Journal of the American Academy Dermatology,* 32(5):S15-S23 (1995).
Lippman et al., "Comparison of Low-Dose Isotretinoin with Beta Carotene to Prevent Oral Carcinogenesis," *The New England Journal of Medicine,* 328(1):15-20, 57-59 (1993).
Lupton et al., "Nonablative Laser Skin Resurfacing Study Using a 1540 nm Erbium Glass Laser: A Clinical and Histologic Analysis," *Dermatol. Surg.,* 28:833-835 (2002).
Maiman, T., "Biomedical Lasers Evolve Toward Clinical Applications," *Hospital Management,* 39-41 (1966).
Margolls et al., "Visible Action Spectrum for Melanin-Specific Selective Photothermolysis," *Lasers in Surgery and Medicine,* 9:389-397 (1989).
Matsumoto, et al., "Ruby Laser Treatment of Melanin Pigmented Skin Lesions Using Toshiba Model LRT-301A Ruby Laser," *Journal of Japanese Society for Laser Surgery and Medicine,* 10(3):451-454 (1989).
Mehrtens, "The Interaction of Light with Skin," University of Canterbury, New Zealand, Masters Thesis (1994).
Mehrtens, "Photothermal Treatment of Cutaneous Lesions," University of Canterbury, New Zealand, Doctor of Philosophy Thesis (2001).
Meloy, T., "The Laser's Bright Magic," *National Geographic,* 858-881(1966).
Mester et al., "Effect of Laser Beam on the Hair Growth of Mice," *Experimental Medicine,* 19:628-631 (1967).
Mester et al., "The Stimulating Effect of Low Power Laser-Rays on Biological Systems," *Laser Review,* 3-6 (1968).
Mester et al., "Effect of Laser Rays on Wound Healing," *The American Journal of Surgery,* 122:532-535 (1971).
Mester et al., "The Biomedical Effects of Laser Application," *Lasers in Surgery and Medicine,* 5:31-39 (1985).
Micozzi et al., "Cartenodermia in Men with Elevated Cartenoid Intake from Foods and β-Carotene Supplements," *The American Journal of Clinical Nutrition,* 48(4):1061-1064 (1988).
Milner et al., "Dynamic Cooling for Spatial Confinement of Laser Induced Thermal Damage in Collagen," Abstract 262, *American Society for Laser Medicine and Surgery* Abstracts (1995).
Miyasaka et al., "Basic and Clinical Studies of Laser for Hyperpigmented Skin Lesions," *Journal of the Japanese Society for Laser Surgery and Medicine,* 11:117-127 (1991).
Mordon et al., "In Vivo Experimental Evaluation of Skin Remodeling by Using an Er:Glass Laser With Contact Cooling," *Lasers in Surgery and Medicine,* 27:1-9 (2000).
Nakaoka et al., "The Square and Uniform Intensity Ruby Laser for the Treatment of Pigmented Skin Lesions," *European Journal of Plastic Surgery,* 15:23-30 (1992).
Nelson et al., "Epidermal Cooling During Pulsed Laser Treatment of Selected Dermatoses," *SPIE,* 2623:32-39 (1995).
Nelson et al., "Dynamic Epidermal Cooling During Pulsed Laser Treatment of Port-Wine Stain," *Arch Dermatol,* vol. 131:(1995).
Nelson et al., "Dynamic Cooling of the Epidermis During Laser Port Wine Stain Therapy," Abstract 253, *American Society for Laser Medicine and Surgery* Abstracts (1994).
Nelson et al., "Dynamic Epidermal Cooling in Conjunction with Laser-Induced Photothermolysis of Port Wine Stain Blood Vessels," *Lasers in Surgery and Medicine,* 19:224-229 (1996).
"New Perspectives on Acne," *Clinician,* 12(2):3-29 (Jul. 1994).
Ngim, "The Burned Ear (I): An Experimental Study with the Rabbit Model to Evaluate Scalding Temperature, Surface and Histopathologic Appearance, and Healing Responses with Depth of Injury," *Annals Academy of Medicine Singapore,* 21(5):597-604 (1992).
Nicolaides, "Skin Lipids: Their Biochemical Uniqueness" *Science,* 186(4158):19-26 (1974).
Ohshiro et al., "The Ruby and Argon Lasers in the Treatment of Naevi," *Annals Academy of Medicine,* 12(2):(1983).
Ohtsuka et al., "Histological Studies and Clinical Experiences of Ruby Laser Treatment," 107-115 (1991).
Orfanos et al., "Oral Retinoids in the Treatment of Seborrhoea and Acne," *Dermatology,* 196(1):140-147 (1998).
Oshry et al., "Argon Green Laser Photoepilation in the Treatment of Trachomatous Trichiasis," *Ophthalmic Plastic and Reconstructive Surgery,* 10(4):253-255 (1994).
Paithankar et al., "Acne Treatment with a 1,450 nm Wavelength Laser and Cryogen Spray Cooling," *Lasers Surg Med.,* 31:106-114 (2002).

(56) References Cited

OTHER PUBLICATIONS

Paithankar et al., "Subsurface Skin Renewal by Treatment with a 1450-nm Laser in Combination with Dynamic Cooling," *J. Biomed Opt.*, 8:545-51 (2003).
Parrish et al., "Selective Thermal Effects with Pulsed Irradiation from Lasers:From Organ to Organelle," *The Journal of Investigative Dermatology*, 80(6):75s-80s (1983).
Peacock, Jr., E., "Structure, Synthesis, and Interaction of Fibrous Protein and Matrix," in *Wound Repair*, 3$^{rd}$ Edition, ed. W.B. Saunders Co., Chapter 4:56-101 (1984).
Pearce, et al., "Rate Process of Analysis of Thermal Damage," in *Optical-Thermal Response of Laser Irradiated Tissue*, eds. Welch, et al., Plenum Press, New York, New York, Chapter 17:561-606 (1995).
Pinkus, "Sebaceous Glands and Acne Vulgaris: Unsolved Problems," *The Journal Investigative Dermatology*, 62(3):336-339 (1974).
Poblet et al., "Cystic Verruciform Xanthoma," *Journal of the American Academy of Dermatology*, 25(2):330-331 (1991).
Polla et al., "Melanosomes Are a Primary Target of Q-Switched Ruby Laser Irradiation in Guinea Pig Skin," *The Journal of Investigative Dermatology*, 89(3):281-286 (1987).
Prince et al., "Increased Preferential Absorption in Human Atherosclerotic Plaque with Oral Beta Carotene," *Circulation*, 78(2):338-344 (1988).
Prince et al., "Rapid Serum Carotene Loading with High-Dose β-Carotene: Clinical Implications," *The Journal of Cardiovascular Pharmacology*, 17(2):343-347 (1991).
Prince et al., (1993) "Beta-Carotene Accumulation in Serum and Skin 1-3, " *The American Journal Clinical Nutrition*, 57(2): 175-181 (1993).
Ramli et al. "Subsurface Tissue Lesions Created Using an Nd:YAG Laser and Cryogen Cooling," *J Endourol.*, 17:923-6 (2003).
Ramli et al., "Subsurface Tissue Lesions Created Using an Nd:YAG Laser and a Sapphire Contact Cooling Probe," *Lasers Surg. Med.*, 35:392-396 (2004).
Raulin et al., "Effective Treatment of Hypertrichosis with Pulsed Light:A Report of Two Cases," *Ann. Plast. Surg.*, 39:169-174 (1997).
Riggle et al., "Laser Effects on Normal and Tumor Tissue," *Laser Applications in Medicine and Biology*, 1:35-65 (1971).
Rosenfeld et al., "Treatment of Cutaneous and Deep Vascular Lesions with the Nd:YAG Laser," *Lasers in Surgery and Medicine*, 6:20-23 (1986).
Rosenfeld et al., "The Treatment of Cutaneous Vascular Lesions with the ND:YAG Laser," *Annals of Plastic Surgery*, 21(3):223-230 (1988).
Schirmer, K., "Simultaneous Thermal and Optical Breakdown Mode Dual Laser Action," *Ophthalmologica*, 205:169-177 (1992).
Shahidullah et al., "Isotretinoin Therapy in Acne Vulgaris: A 10-Year Retrospective Study in Singapore," *International Journal of Dermatology*, 33(1):60-63 (1994).
Shapiro et al., "Kinetic Characteristics of β-Carotene Uptake and Depletion in Rat Tissue," *The Journal of Nutrition*, 114(10):1924-1933 (1984).
Sherwood et al., "Effect of Wavelength on Cutaneous Pigment Using Pulsed Irradiation," *The Journal of Investigative Dermatology*, 92(5):717-720 (1989).
Sherwood et al., "Improved Staining Method for Determining the Extent of Thermal Damage to Cells," *Lasers Surg Med.*, (Dec. 12, 2006).
Shimbashi et al., "Ruby Laser Treatment of Pigmented Skin Lesions," *Aesthetic Plastic Surgery*, 19:225-229 (1995).
Solomon et al., "Histopathology of the Laser Treatment of Port-Wine Lesions: Biopsy Studies of Treated Areas Observed up to Three Years After Laser Impacts," *The Journal of Investigative Dermatology*, 50(2):141-146 (1968).
Prince et al., (1993) "Beta-Carotene Accumulation in Serum and Skin 1-3," *The American Journal Clinical Nutrition*, 57(2): 175-181 (1993).
Stathakis et al., "Descriptive Epidemiology of Acne Vulgaris in the Community," *Australasian Journal of Dermatology*, 38(3):115-123 (1997).
Sternberg et al., "Porphyrin-based Photosensitizers for Use in Photodynamic Therapy," *Tetrahedron*, 54:4151-4202 (1998).
Stewart, "Sebaceous Gland Lipids," *Seminars in Dermatology*, 11(2):100-105 (1992).
Strauss, "The Sebaceous Glands: Twenty-Five Years of Progress" *The Journal of Investigation Dermatology*, 67(1):90-97 (1976).
Svaasand et al., "Melanosomal Heating During Laser Induce Photothermolysis of Port Wine Stains," Abstract 233, *American Society for Laser Medicine and Surgery* Abstracts (1995).
Svaasand et al., "Epidermal Heating During Laser Induced Photothermolysis of Port Wine Stains: Modeling Melanosomal Heating After Dynamic Cooling the Skin Surface," *SPIE*, 2323:366-377 (1994).
Sykes, "Acne: A Review of Optimum Treatment," *Drugs*, 48(1):59-70 (1994).
Takata et al., "Laser-Induced Thermal Damage of Skin," SAM-TR-77-38, USAF School of Aerospace Medicine (1977).
Tanino et al., "Development of Ruby Laser System for Medical Use," (Abstract) *Journal of the Japanese Society for Laser Surgery and Medicine*, 11(4):93-98 (1991).
Taub et al., "Multicenter Clinical Perspectives on a Broadband Infrared Light Device for Skin Tightening," *J. Drugs Dermatol.*, 5:771-778 (2006).
Taylor et al., "Treatment of Tattoos by Q-Switched Ruby Laser," *Arch. Dermatol.*, 126:893-899 (1990).
"Tech News: Lasers and Hair," *Circle 21*, (1983).
Thomsen et al., "Changes in Birefringence as Markers of Thermal Damage in Tissues," *IEE, Transaction on Biomedical Engineering*, 36(12):1174-1179 (1989).
Thomsen, S., "Pathologic Analysis of Photothermal and Photomechanical Effects of Laser-tissue Interactions," *Photochemistry and Photobiology*, 53(6):825-835 (1991).
Tosti, "A Comparison of the Histodynamics of Sebaceous Glands and Epidermis in Man: A Microanatomic and Morphometric Study," *The Journal of Investigative Dermatology*, 62(3):147-152 (1974).
Turkington et al., "Skin Deep: An A-Z of Skin Disorders, Treatment and Health," *Facts on File, Inc.*, New York, pp. 7-9 (1996).
van Gernert et al., "Is There an Optimal Laser Treatment for Port Wine Stains?," *Lasers in Surgery and Medicine*, 6:76-83 (1986).
van Gernert et al., "Limitations of Carbon Dioxide Lasers for Treatment of Port Wine Stains," *Arch. Derm.*, 123:71-73 (1987).
van Gernert et al., "Temperature Behavior of a Model Port Wine Stain During Argon Laser Coagulation," *Phys. Med. Biol.*, 27(9):1089-1104 (1982).
Waldman et al., "Cutaneous Inflammation: Effects of Hydroxy Acids and Eicosanoid Inhibitors on Vascular Permeability," Abstracts 523, 88(4):(1987).
Wang et al., "Characterization of Human Scalp Hairs by Optical Low-Coherence Reflectometry," *Optics Letters*, 20(6):524-526 (1995).
Wang et al., "MCML—Monte Carlo Modeling of Photon Transport in Multi-Layered Tissues," *Computer Methods and Programs in Biomedicine*, 47:131-146 (1995).
Warren et al., "Pigmentation Induction by Melanocyte Stimulating Hormone in Human Skin Culture," Abstracts 523, 88(4):(1987).
Wastek et al., "Characterization of H-Substance P (SP) Binding to a Mouse Monoclonal Mast Cell Line (MC/9)," Abstracts 523, 88(4):(1987).
Watanabe et al., "The Effect of Pulse Duration on Selective Pigmented Cell Injury by Dye Lasers," Abstracts 523, 88(4):(1987).
Watanabe et al., "Comparative Studies of Femtosecond to Microsecond Laser Pulses on Selective Pigmented Cell Injury in Skin," *Photochemistry and Photobiology*, 53(6):757-761 (1991).
Weaver et al., "Mathematical Model of Skin Exposed to Thermal Radiation," *Aerospace Medicine*, 40(1):24-30 (1969).
Weinstein, "Cell Kinetics of Human Sebaceous Glands," *The Journal of Investigative Dermatology*, 62(3):144-146 (1974).
Weissman et al., "Growth, Collagen and Glycosaminoglcan Synthesis by Dermal Fibroblasts Derived From Puva Treated and Psoriatic Patients," Abstracts 523, 88(4):(1987).

(56) References Cited

OTHER PUBLICATIONS

Welch et al., "Evaluation of Cooling Techniques for the Protection of the Epidermis During ND-YAG Laser Irradiation of Skin," in *Neodymium-YAG Laser in Medicine and Surgery*, ed. SN Joffe, Elsevier, New York (1983).

Welch et al., "Clinical Use of Laser-Tissue Interactions," *IEEE Engineering in Medicine and Biology Magazine*, pp. 10-13 (1989).

Werse et al., "Effects of Essential Fatty Acid Deficiency on the Structure and Function of Epidermal Lipids," Abstracts 523, 88(4):(1987).

Williford et al., "The Spectrum of Normolipemic Plane Xanthoma," *The American Journal of Dermatopathology*, 15(6):572-575 (1993).

"Workshop on Analysis of Laser-Tissue Interaction for Clinical Treatment," University of Texas, Austin, TX 78712, Jul. 14-18, 1986.

Yules et al., "The Effect of Q-Switched Ruby Laser Radiation on Dermal Tattoo Pigment in Man," *Arch. Surg.*, 95:179-180 (1967).

Zhang, "High Power Flashlamps in Dermatology," University of Canterbury, New Zealand, Masters Thesis, 1993.

Zeitler et al., "Laser Characteristics that Might be Useful in Biology," *Laser Applications in Medicine and Biology*, 1:1-18 (1971).

* cited by examiner

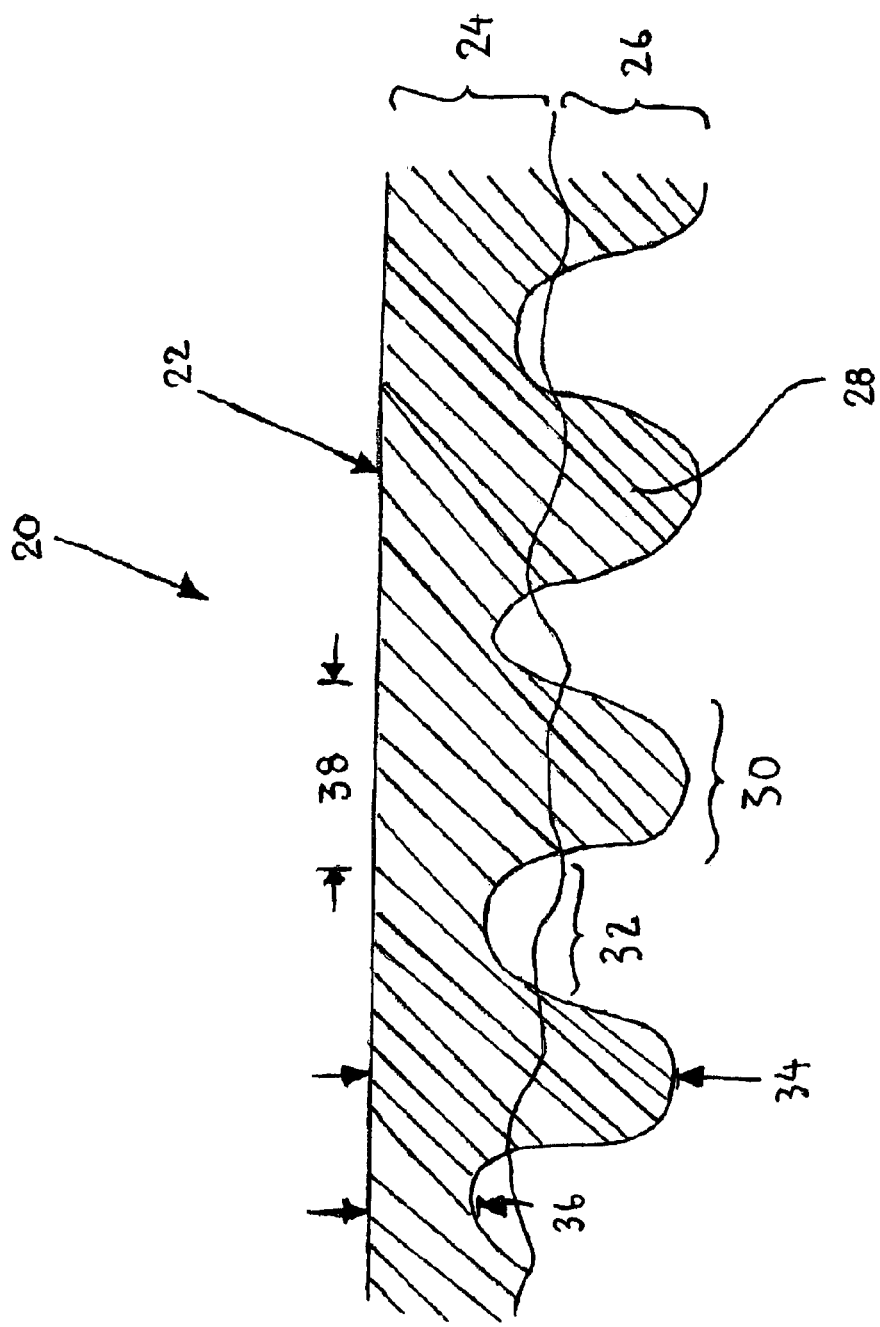

TREATMENT OF SKIN BY SPATIAL MODULATION OF THERMAL HEATING

CROSS-REFERENCE TO RELATED APPLICATION

This application is a divisional application of U.S. patent application Ser. No. 11/763,111 filed Jun. 14, 2007, now U.S. Pat. No. 8,246,611, which claims the benefit of and priority to U.S. Provisional Application Ser. No. 60/813,729 filed Jun. 14, 2006, both of which are owned by the assignee of the instant application and the disclosures of which are incorporated herein by reference in their entireties.

FIELD OF THE INVENTION

The invention relates generally to a skin treatment using radiation. In particular, the invention relates to a method for treating skin using a beam of radiation to cause spatially modulated thermal injury of the skin sufficient to elicit a healing response and improvement in the skin.

BACKGROUND OF THE INVENTION

Ablative resurfacing of skin with lasers can be an effective treatment for skin conditions such as wrinkles. However, ablative resurfacing can have undesirable post-treatment side effects. For example, crusting, oozing, erythema can last up to 5 weeks. Furthermore, permanent scarring is a possible long-term side effect of ablative resurfacing. Such side effects can be a deterrent to individuals who otherwise desire treatment.

Improved treatments with reduced side effects include forming sub-surface thermal damage of skin, while leaving the top layer intact by combining heating and surface cooling. However, the results of sub-surface methods can be less dramatic than those achieved by ablative resurfacing. Other improvements include fractional resurfacing techniques, that treat skin in discrete spots and leave the skin between the spots untreated.

Fractional resurfacing technologies can have advantages including lower incidences of side-effects and expedited healing. These advantages can result from the undamaged regions providing blood and nutrients to the adjacent damaged regions and accelerating the healing process. Ablative resurfacing and technologies that include inducing uniform damage corresponding to coverage of an entire region can include higher efficacy at the cost of increased side effects.

SUMMARY OF THE INVENTION

The invention, in various embodiments, combines many of the advantages of ablative resurfacing with those of fractional methods. Skin can be treated by delivering a beam of radiation to a target region to cause a zone of thermal injury. The zone can include a lateral pattern of varying depths of thermal injury distributed along the target region. The lateral pattern can include at least one first sub-zone of a first depth of thermal injury laterally adjacent to at least one second sub-zone of a second depth of thermal injury. The at least one first sub-zone of the first depth and the at least one second sub-zone of the second depth can extend from a surface of the target region of the skin to form a substantially continuous surface thermal injury.

A beam of radiation can have a modulated spatial profile such that the fluence, the intensity, and/or the wavelength delivered to the skin can be varied. The spatial profile determines the depth of thermal injury to the skin. A beam of radiation can be delivered to a region of skin to cause modulated spatial profile of temperature, such that the depth of damage to the skin is varied. An advantage of the invention is that a large target region can be formed with damaged regions adjacent to substantially undamaged regions within the target region, together with a substantially continuous surface thermal injury. The substantially undamaged regions can be undamaged or less damaged than the damaged regions. Other advantages include: improved treatment efficacy initiating from zones corresponding to deeper first damage zones, high coverage of a treatment region corresponding to deeper first damage zones and less deep second damage zones, improved efficacy relating to forming a substantially continuous surface thermal injury, and improved post-treatment healing initiating from zones corresponding to less deep second damage zones.

In one embodiment, the treatment can be used to treat wrinkles or for skin rejuvenation. However, the treatment is not limited to treating wrinkles or skin rejuvenation. A beam of radiation can be delivered non-invasively to affect the skin.

In one aspect, the invention features a method for treating skin including delivering a beam of radiation to a target region of the skin, to cause a zone of thermal injury including a lateral pattern of varying depths of thermal injury distributed along the target region. The lateral pattern includes at least one first sub-zone of a first depth of thermal injury laterally adjacent to at least one second sub-zone of a second depth of thermal injury. The first depth is greater than the second depth. The at least one first sub-zone of the first depth and the at least one second sub-zone of the second depth extend from a surface of the target region of the skin to form a substantially continuous surface thermal injury. Both the at least one first sub-zone of the first depth and the at least one second sub-zone of the second depth are substantially heated to at least a critical temperature to cause the thermal injury.

In another aspect, the invention features a method for treating skin including delivering a beam of radiation to a first portion of a target region of the skin, to heat the first portion to at least a critical temperature to cause a first thermal injury. The method also includes translating the beam of radiation to a second portion of the target region. Additionally, the method includes delivering the beam of radiation to the second portion of the target region, to heat the second portion to at least the critical temperature to cause a second thermal injury. The first thermal injury and the second thermal injury extend from a surface of the target region of the skin to form a substantially continuous surface thermal injury and form a lateral pattern of varying depths of thermal injury distributed along the target region.

In yet another aspect, the invention features an apparatus for treating skin including a source of a beam of radiation and a modulator. The modulator receives the beam of radiation and forms a modulated spatial profile of the beam including a first plurality of first regions at a first fluence and a second plurality of second regions at a second fluence. The first fluence is greater than the second fluence, and each first region is spaced from an adjacent first region by a respective second region. The apparatus also includes a device for delivering the beam of radiation to a target region of skin to cause a zone of thermal injury including a lateral pattern of varying depths of thermal injury distributed along the target region. The lateral pattern includes at least one first sub-zone of a first depth of thermal injury laterally adjacent to at least one second sub-zone of a second depth of thermal injury.

The first depth is greater than the second depth. The at least one first sub-zone of the first depth and the at least one second sub-zone of the second depth extend from a surface of the target region of the skin to form a substantially continuous surface thermal injury. The at least one first sub-zone of the first depth and the at least one second sub-zone of the second depth are substantially heated to at least a critical temperature to cause the thermal injury.

In other examples, any of the aspects above, or any apparatus or method described herein, can include one or more of the following features.

In various embodiments, the lateral pattern has a substantially sinusoidal cross sectional injury profile. The method can include delivering the beam of radiation to the target region to form a one-dimensional lateral pattern of varying depths of thermal injury. The method can include delivering the beam of radiation to the target region to form a two-dimensional lateral pattern of varying depths of thermal injury. The first depth and the second depth can be between about 2 mm and about 0.02 mm. The first depth can be about 1.5 mm and the second depth can be about 0.05 mm.

In some embodiments, the critical temperature is below about 100° C., 95° C., 90° C., 85° C., 80° C., 75° C., 70° C., 65° C., 60° C., 55° C., or 50° C. The thermal injury can include at least one of ablation, coagulation, necrosis, and acute thermal injury of skin. The method can include heating the at least one first sub-zone and the at least one second sub-zone to substantially the same temperature.

In certain embodiments, the method includes cooling the surface of the skin, to control the surface thermal injury. The method can include cooling the surface of the skin, to prevent unwanted surface thermal injury. The method can include cooling the target region of skin to produce at least one first region at a first temperature and at least one second region at a second temperature, the first temperature being greater than the second temperature, the at least one first region corresponding to the at least one first sub-zone, and the at least one second region corresponding to the at least one second sub-zone. The method can include cooling the target region of skin to produce at least one first region cooled to a first depth and at least one second region cooled to a second depth, the first depth being less than the second depth, the at least one first region corresponding to the at least one first sub-zone, and the at least one second region corresponding to the at least one second sub-zone.

In various embodiments, the method includes delivering a beam of radiation having a first wavelength to the at least one first sub-zone to cause the first depth of thermal injury and a beam of radiation having a second wavelength to the at least one second sub-zone to cause the second depth of thermal injury. The method can include delivering a beam of radiation having a first fluence to the at least one first sub-zone to cause the first depth of thermal injury and a beam of radiation having a second fluence to the at least one second sub-zone to cause the second depth of thermal injury. The method can include delivering a beam of radiation having a first pulse duration to the at least one first sub-zone to cause the first depth of thermal injury and a beam of radiation having a pulse duration to the at least one second sub-zone to cause the second depth of thermal injury.

In some embodiments, the at least two first sub zones of the first depth are separated by a center to center distance of about 0.05 mm to about 20 mm. The at least one first sub-zone of the first depth can have an aspect ratio of diameter:depth up to about 0.1:10. The at least one second sub-zone of the second depth can have an aspect ratio of diameter:depth up to about 0.1:10.

In certain embodiments, the apparatus includes a cooling system for controllably cooling at least a portion of the target region of skin, to control the thermal injury within the target region. The apparatus can include a cooling system for cooling the target region of skin to produce at least one first region at a first temperature and at least one second region at a second temperature, the first temperature being greater than the second temperature, the at least one first region corresponding to the at least one first sub-zone, and the at least one second region corresponding to the at least one second sub-zone. In one embodiment, the apparatus includes a cooling system for cooling the target region of skin to produce at least one first region cooled to a first depth and at least one second region cooled to a second depth, the first depth being less than the second depth, the at least one first region corresponding to the at least one first sub-zone, and the at least one second region corresponding to the at least one second sub-zone.

Other aspects and advantages of the invention can become apparent from the following drawings and description, all of which illustrate the principles of the invention, by way of example only.

BRIEF DESCRIPTION OF THE DRAWINGS

The advantages of the invention described above, together with further advantages, may be better understood by referring to the following description taken in conjunction with the accompanying drawings. The drawings are not necessarily to scale, emphasis instead generally being placed upon illustrating the principles of the invention.

FIGS. 3A-3B show views of an exemplary cross-section of a region of skin.

DESCRIPTION OF THE INVENTION

Figure 1:
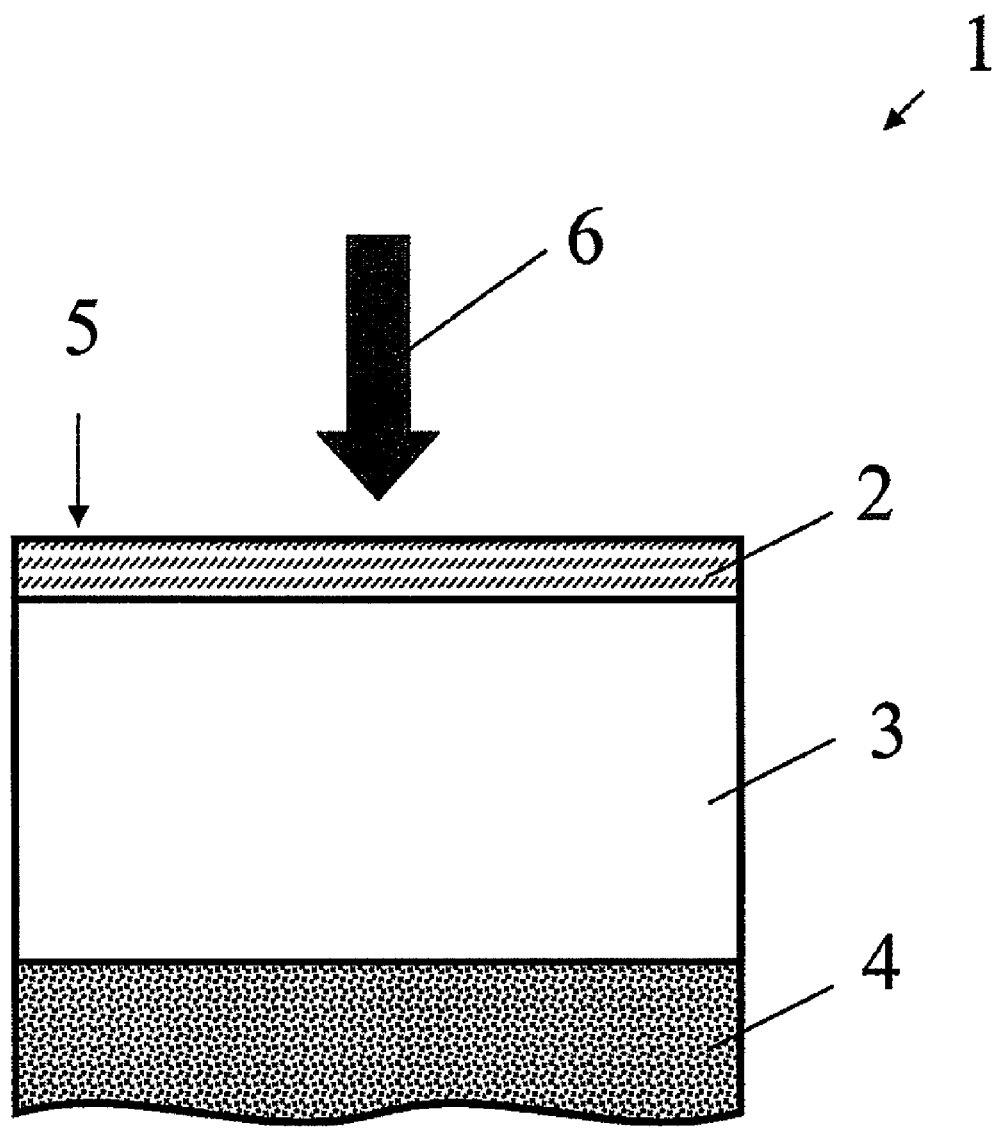
FIG. 1 shows an exemplary cross-section of skin.

FIG. 1 shows an exemplary cross-section of skin 1 including a region of epidermis 2, a region of dermis 3, a region of subcutaneous tissue 4, and a surface of the skin 5. In one embodiment, the skin 1 can be a region of human skin with wrinkles. A beam of radiation 6 can be delivered to the skin 1 to treat at least a region of skin, including a region of epidermis 2 and/or a region of dermis 3. Skin treatments can include skin rejuvenation and treatments for wrinkles, vessels, pigmentation, scarring, and acne.

A therapeutic injury can be induced with electromagnetic radiation in the visible to infrared spectral region. A wavelength of light that penetrates into at least a portion of skin can be used. Chromophores can include blood (e.g., oxyhemoglobin and deoxyhemoglobin), collagen, melanin, fatty tissue, and water. Light sources can include lasers, light emitting diodes, or an incoherent source, and can be either pulsed or continuous. In one embodiment, a light source can be coupled to a flexible optical fiber or light guide, which can be introduced proximally to a target region skin. The light source can operate at a wavelength with depth of penetration into skin that is less than the thickness of the target region of skin.

In various embodiments, skin in a target region is heated to a critical temperature to cause thermal injury. In certain embodiments, the critical temperature is below about 100° C. In other embodiments, the critical temperature is below about 95° C., 90° C., 85° C., 80° C., 75° C., 70° C., 65° C., 60° C., 55° C., or 50° C. In one embodiment, the critical temperature is the temperature associated with ablation, coagulation, necrosis, and/or acute thermal injury of skin.

Figure 2:
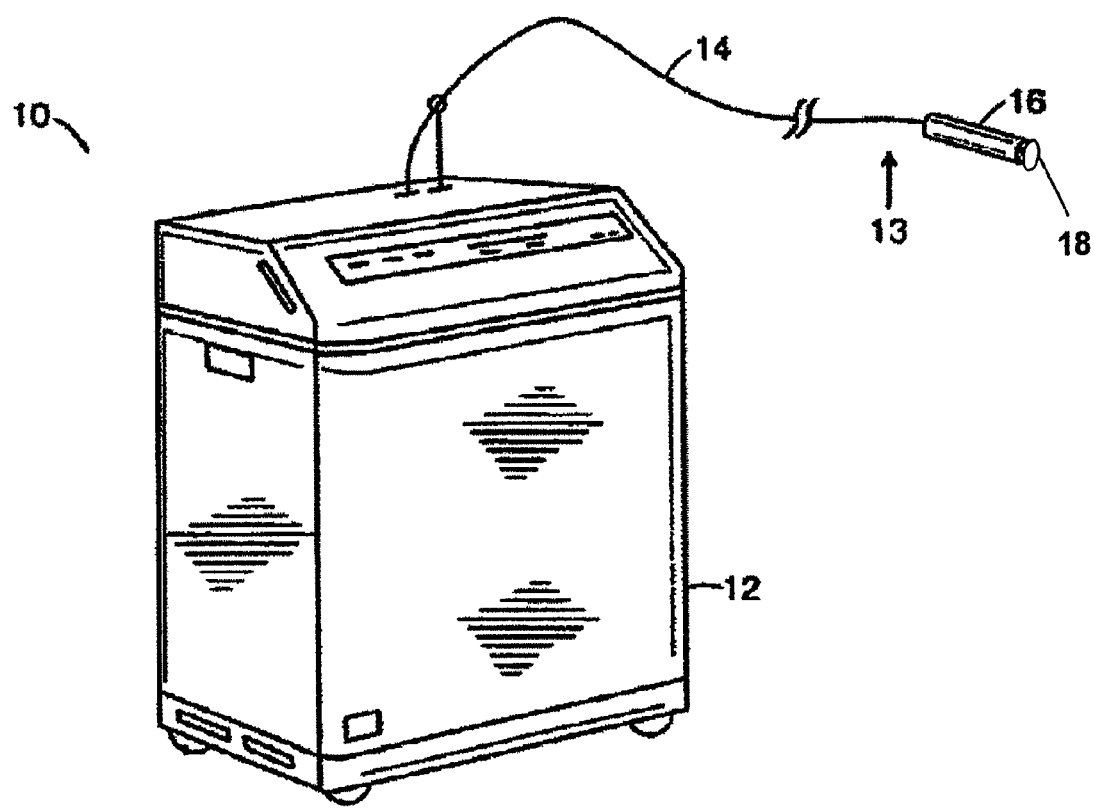
FIG. 2 shows an exemplary embodiment of a system for treating skin.

FIG. 2 shows an exemplary embodiment of a system 10 for treating skin. The system 10 can be used to non-invasively deliver a beam of radiation to a target region of skin. The system 10 includes an energy source 12 and a delivery system 13. In one embodiment, a beam of radiation provided by the energy source 12 is directed via the delivery system 13 to a target area. In the illustrated embodiment, the delivery system 13 includes a fiber 14 having a circular cross-section and a handpiece 16. A beam of radiation can be delivered by the fiber 14 to the handpiece 16, which can include an optical system (e.g., an optic or system of optics) to direct the beam of radiation to the target area. A user can hold or manipulate the handpiece 16 to irradiate the target area. The handpiece 16 can be positioned in contact with a skin surface, can be positioned adjacent a skin surface, can be positioned proximate a skin surface, can be positioned spaced from a skin surface, or a combination of the aforementioned. In the embodiment shown, the handpiece 16 includes a spacer 18 to space the delivery system 13 from the skin surface. In one embodiment, the spacer 18 can be a distance gauge, which can aid a practitioner with placement of the handpiece 16.

In various embodiments, the energy source 12 can be an incoherent light source, a coherent light source (e.g., a laser), a solid state laser, a diode laser, a fiber coupled diode laser array, an optically combined diode laser array, and/or a high power semiconductor laser. In some embodiments, two or more sources can be used together to effect a treatment. For example, an incoherent source can be used to provide a first beam of radiation while a coherent source provides a second beam of radiation. The first and second beams of radiation can share a common wavelength or can have different wavelengths. In an embodiment using an incoherent light source or a coherent light source, the beam of radiation can be a pulsed beam, a scanned beam, or a gated continuous wave (CW) beam.

In various embodiments, the source of electromagnetic radiation can include a fluorescent pulsed light (FPL) or an intense pulsed light (IPL) system. For example, the system can be a LIGHTSTATION™ (by Candela Corporation of Wayland, Mass.), or an OMNILIGHT™, NOVALIGHT™, or PLASMALITE™ system (by American Medical Bio Care of Newport Beach, Calif.). However, the source of electromagnetic radiation can also include a laser, a diode, a coherent light source, an incoherent light source, or any other source of electromagnetic radiation. FPL technologies can utilize laser-dye impregnated polymer filters to convert unwanted energy from a xenon flashlamp into wavelengths that enhance the effectiveness of the intended applications. FPL technologies can be more energy efficient and can generate significantly less heat than comparative IPL systems. A FPL system can be adapted to operate as a multi-purpose treatment system by changing filters or handpieces to perform different procedures. For example, separate handpieces allow a practitioner to perform tattoo removal and other vascular treatments. An exemplary FPL system is described in U.S. Pat. No. 5,320,618, the disclosure of which is herein incorporated by reference in its entirety.

In various embodiments, the beam of radiation can have a wavelength between about 380 nm and about 2600 nm. In certain embodiments, the beam of radiation can have a wavelength between about 1,200 nm and about 2,600 nm, between about 1,200 nm and about 1,800 nm, or between about 1,300 nm and about 1,600 nm. In one embodiment, the beam of radiation has a wavelength of about 1,500 nm. In other embodiments, the beam of radiation has a wavelength up to about 2,100 nm or up to about 2,200 nm.

In various embodiments, the beam of radiation can have a fluence of about 1 J/cm$^2$ to about 500 J/cm$^2$. For a given wavelength of radiation, a range of effective fluences can be approximated. Because radiation of wavelength between about 380 nm and about 2600 nm is absorbed by water, and because skin is about 70% water, the absorption coefficient of skin can be approximated as 70% of the absorption coefficient of water. Because the absorption coefficient of water is a function of the wavelength of radiation, the desired fluence depends on the chosen wavelength of radiation. The fluence necessary to produce a desired damage depth can be approximated as the fluence that will raise the temperature to the critical temperature at the desired penetration depth, calculated as:

$$\lceil 3 * \mu_a * (\mu_a + \mu_s(1-g))^{-0.5}$$

where $\mu_a$, $\mu_s$, and g are absorption coefficient, scattering coefficient, and the anisotropy factor of skin, respectively.

TABLE 1

Approximate fluence range to produce a first sub-zone of damage using a given wavelength.

| Wavelength (nm) | Fluence (J/cm$^2$) |
|---|---|
| 1180 | 100-498 |
| 1200 | 100-498 |
| 1220 | 109-545 |
| 1240 | 118-588 |
| 1260 | 116-582 |
| 1280 | 106-528 |
| 1300 | 93-466 |
| 1320 | 75-375 |
| 1340 | 65-326 |
| 1360 | 56-280 |
| 1380 | 29-146 |
| 1400 | 19-96 |
| 1420 | 14-70 |
| 1440 | 11-54 |
| 1460 | 11-55 |
| 1480 | 15-73 |
| 1500 | 18-88 |
| 1520 | 22-111 |
| 1540 | 20-101 |
| 1560 | 23-115 |
| 1580 | 26-130 |
| 1600 | 26-132 |
| 1620 | 31-153 |
| 1640 | 36-178 |
| 1660 | 39-196 |

TABLE 1-continued

Approximate fluence range to produce a first sub-zone of damage using a given wavelength.

| Wavelength (nm) | Fluence (J/cm²) |
|---|---|
| 1680 | 40-198 |
| 1700 | 40-200 |
| 1720 | 35-174 |
| 1740 | 29-145 |
| 1760 | 25-124 |
| 1780 | 26-128 |
| 1800 | 26-129 |
| 1820 | 23-115 |
| 1840 | 23-117 |
| 1860 | 22-109 |
| 1880 | 10-50 |
| 1900 | 5-23 |
| 1920 | 3-14 |
| 1940 | 3-13 |
| 1960 | 3-15 |
| 1980 | 3-17 |
| 2000 | 4-22 |
| 2020 | 6-28 |
| 2040 | 7-35 |
| 2060 | 8-40 |
| 2080 | 10-49 |
| 2100 | 12-58 |
| 2120 | 13-65 |
| 2140 | 15-76 |
| 2160 | 17-83 |
| 2180 | 18-90 |
| 2200 | 19-94 |
| 2220 | 19-96 |
| 2240 | 19-94 |
| 2260 | 18-90 |
| 2280 | 16-78 |
| 2300 | 14-69 |
| 2320 | 12-58 |
| 2340 | 10-49 |
| 2360 | 8-42 |
| 2380 | 7-36 |
| 2400 | 6-31 |
| 2420 | 5-26 |
| 2440 | 5-23 |
| 2460 | 4-20 |
| 2480 | 4-18 |
| 2500 | 3-17 |
| 2520 | 3-15 |
| 2540 | 3-14 |
| 2560 | 3-13 |
| 2580 | 2-12 |
| 2600 | 2-10 |

In various embodiments, the fluence used to produce a second sub-zone of damage is less than the fluence used to produce a first sub-zone of damage. In certain embodiments, the fluence used to produce a second sub-zone of damage is about 10% of the fluence used to produce a first sub-zone of damage.

In various embodiments, a desired penetration depth of light into the skin (and a corresponding depth of thermal injury) can be targeted by selecting a wavelength of a beam of radiation. For example, a water absorption coefficient can be taken from G. M. Hale and M. R. Querry, "Optical constants of water in the 200 nm to 200 μm wavelength region," Appl. Opt., 12, 555-563, (1973) and an Optical Penetration Depth (OPD) can be calculated using a diffusion approximation. As described above, $\mu_a$ of skin is taken as $\mu_a$ of water multiplied by 0.7. The product of scattering coefficient and (1-anisotropy factor) is taken as 12 cm$^{-1}$.

TABLE 2

Approximate wavelength for a corresponding desired penetration depth.

| lambda (nm) | OPD (microns) | OPD (mm) |
|---|---|---|
| 1180 | 1896.68 | 1.90 |
| 1200 | 1896.68 | 1.90 |
| 1220 | 1989.42 | 1.99 |
| 1240 | 2071.04 | 2.07 |
| 1260 | 2058.80 | 2.06 |
| 1280 | 1957.11 | 1.96 |
| 1300 | 1832.38 | 1.83 |
| 1320 | 1631.35 | 1.63 |
| 1340 | 1399.75 | 1.40 |
| 1360 | 1110.54 | 1.11 |
| 1380 | 692.68 | 0.69 |
| 1400 | 431.17 | 0.43 |
| 1420 | 279.87 | 0.28 |
| 1440 | 226.74 | 0.23 |
| 1460 | 229.34 | 0.23 |
| 1480 | 288.97 | 0.29 |
| 1500 | 333.69 | 0.33 |
| 1520 | 393.98 | 0.39 |
| 1540 | 445.51 | 0.45 |
| 1560 | 512.22 | 0.51 |
| 1580 | 583.96 | 0.58 |
| 1600 | 651.32 | 0.65 |
| 1620 | 713.46 | 0.71 |
| 1640 | 785.79 | 0.79 |
| 1660 | 831.29 | 0.83 |
| 1680 | 836.88 | 0.84 |
| 1700 | 842.55 | 0.84 |
| 1720 | 773.46 | 0.77 |
| 1740 | 689.83 | 0.69 |
| 1760 | 626.39 | 0.63 |
| 1780 | 575.87 | 0.58 |
| 1800 | 580.12 | 0.58 |
| 1820 | 538.51 | 0.54 |
| 1840 | 492.55 | 0.49 |
| 1860 | 391.16 | 0.39 |
| 1880 | 213.05 | 0.21 |
| 1900 | 111.13 | 0.11 |
| 1920 | 67.16 | 0.07 |
| 1940 | 64.38 | 0.06 |
| 1960 | 72.32 | 0.07 |
| 1980 | 82.28 | 0.08 |
| 2000 | 106.81 | 0.11 |
| 2020 | 128.89 | 0.13 |
| 2040 | 156.06 | 0.16 |
| 2060 | 176.11 | 0.18 |
| 2080 | 211.15 | 0.21 |
| 2100 | 239.41 | 0.24 |
| 2120 | 262.39 | 0.26 |
| 2140 | 296.35 | 0.30 |
| 2160 | 319.62 | 0.32 |
| 2180 | 338.03 | 0.34 |
| 2200 | 349.91 | 0.35 |
| 2220 | 356.02 | 0.36 |
| 2240 | 349.28 | 0.35 |
| 2260 | 338.77 | 0.34 |
| 2280 | 304.49 | 0.30 |
| 2300 | 277.13 | 0.28 |
| 2320 | 240.27 | 0.24 |
| 2340 | 208.26 | 0.21 |
| 2360 | 183.15 | 0.18 |
| 2380 | 161.22 | 0.16 |
| 2400 | 142.20 | 0.14 |
| 2420 | 121.74 | 0.12 |
| 2440 | 109.92 | 0.11 |
| 2460 | 97.31 | 0.10 |
| 2480 | 87.44 | 0.09 |
| 2500 | 83.58 | 0.08 |
| 2520 | 74.66 | 0.07 |
| 2540 | 70.44 | 0.07 |
| 2560 | 66.71 | 0.07 |
| 2580 | 58.99 | 0.06 |
| 2600 | 51.05 | 0.05 |

FIG. 3A shows an exemplary cross-section 20 of a region of skin including a region of skin surface 22, a region of epidermis 24, a region of dermis 26, and a zone of thermal injury 28 including a pattern of varying depths of thermal injury. The pattern includes at least one first sub-zone 30 of a first depth of thermal injury adjacent to at least one second sub-zone 32 of a second depth of thermal injury. The first depth is greater than the second depth. In various embodiments, the depth 34 of thermal injury in the first sub-zone can be measured from the skin surface 22. In various embodiments, the depth 36 of thermal injury in the second sub-zone can be measured from the skin surface 22. In various embodiments, the diameter 38 of thermal injury in a sub-zone can be measured on the skin surface 22.

The at least one first sub-zone 30 of the first depth of thermal injury and the at least one second sub-zone 32 of the second depth of thermal injury extend from the surface 22 of the target region to form a substantially continuous surface thermal injury. The at least one first sub-zone 30 of the first depth and the at least one second sub-zone 32 of the second depth are substantially heated to at least a critical temperature to cause the thermal injury. In one embodiment, the temperature within the at least one first sub-zone 30 of the first depth and the at least one second sub-zone 32 can vary at or above the critical temperature and, accordingly, the degree of thermal injury can also vary at or above a pre-determined amount. In another embodiment, the temperature within the at least one first sub-zone 30 of the first depth and the at least one second sub-zone 32 can be substantially the same and, accordingly, the degree of thermal injury can also be substantially the same.

Figure 3B:
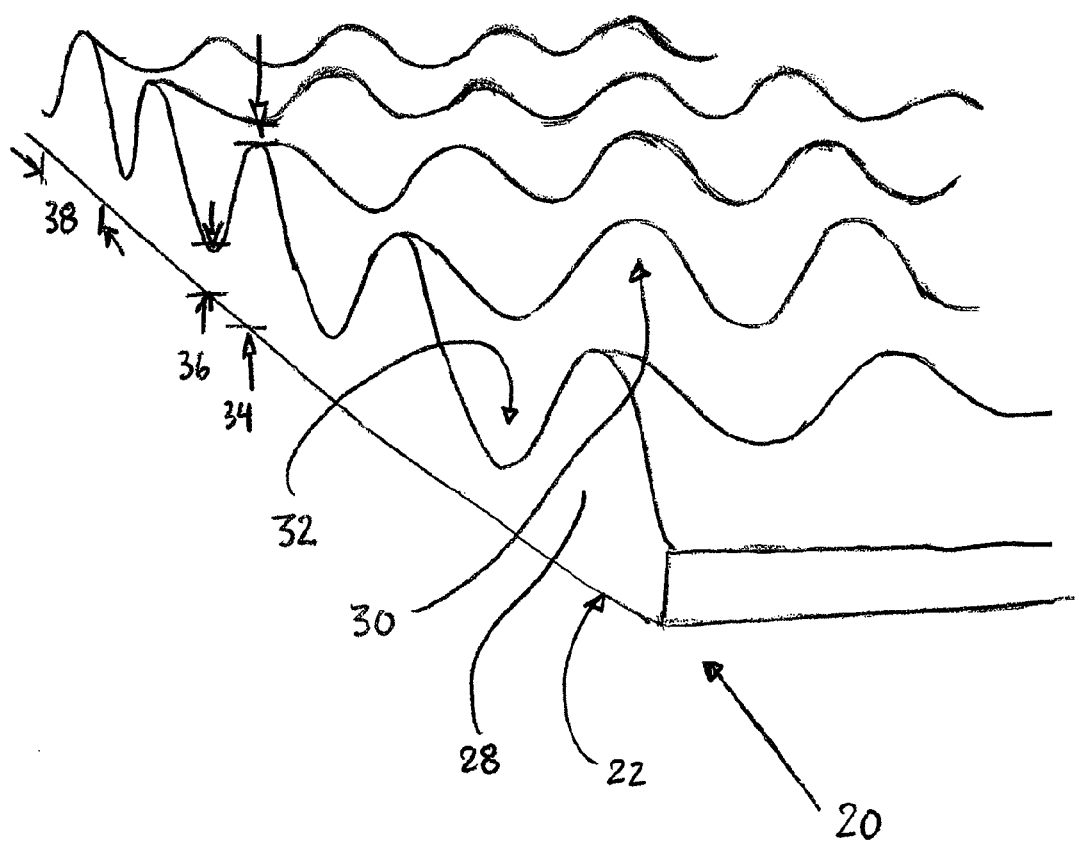

FIG. 3B shows a three-dimensional view of the cross-section 20 of the region of skin in FIG. 3A, including the region of skin surface 22 and a three-dimensional zone of thermal injury 28 including a pattern of varying depths of thermal injury. The exemplary pattern of varying depths of thermal injury is distributed contiguously along the surface 22 of the target region and includes a three-dimensional zone of thermal injury 28 having a pattern with the three-dimensional first sub-zone 30 of a first depth of thermal injury contiguous along the skin surface with the three-dimensional second sub-zone 32 of a second depth of thermal injury. In various embodiments, the depth 34 of thermal injury in the first sub-zone can be measured from the skin surface 22. In various embodiments, the depth 36 of thermal injury in the second sub-zone can be measured from the skin surface 22. In various embodiments, the diameter 38 of thermal injury in a sub-zone can be measured on the skin surface 22.

A first sub-zone of a first depth of thermal injury can improve the efficacy of treatment by including an acute thermal injury. A substantially continuous surface thermal injury can improve the efficacy of treatment by including surface ablation and/or inducing a surface peel. A second sub-zone of a second depth of thermal injury can improve post-treatment healing of skin. A second sub-zone of a second depth of thermal injury can improve post-treatment healing of an adjacent first sub-zone of a first depth of thermal injury. In various embodiments, treatment efficacy can be improved by forming first sub-zones of thermal injury adjacent to second sub-zones of thermal injury. In some embodiments, treatment efficacy can be improved by forming first sub-zones of thermal injury underlying a substantially continuous surface thermal injury. In certain embodiments, post-procedure healing can be improved by improved flow of blood and nutrients provided by a second sub-zone.

In various embodiments, a sub-zone of thermal damage can include a three-dimensional region of epidermis and/or a region of dermis. For example, in certain embodiments, a first sub-zone can include three-dimensional regions of epidermis and dermis, while a second sub-zone can include three-dimensional regions of epidermis.

In various embodiments, the pattern of thermal injury can be a continuously varying pattern (e.g., a sinusoidal-like or wave-like pattern when viewed in two-dimensions or an "egg carton" like pattern when viewed in three-dimensions). In some embodiments, the pattern of thermal injury can be a continuous surface injury with periodic or irregular regions of deeper thermal injury (e.g., a step-function like pattern when viewed in two dimensions). However, the pattern of thermal injury is not limited to any specific design. Contiguous regions in skin of subsurface injury without surface injury can be overlaid by discrete regions of added surface injury. In certain embodiments, contiguous regions of superficial injury can be overlaid by discrete regions of superficial tissue ablation.

In some embodiments, a three-dimensional pattern of varying depths and/or varying severity of thermal injury within skin can be formed. Regions of more deeply and/or severely injured skin can be contiguous with regions of less deeply and/or severely damaged skin. In certain embodiments, first regions of skin with sub-surface injury and without surface injury are formed. Such first regions can be contiguous with second regions of skin without sub-surface injury and with surface injury. In various embodiments, wounds in the skin that require long recovery periods are avoided. For example, effective treatment of skin can be provided without forming large or contiguous areas of acute injury or necrosis.

As a beam or radiation penetrates skin, the fluence ($J/cm^2$) decreases in an approximately exponential fashion. The rate of decrease in fluence is dependent upon the absorption and scattering properties of skin. A local temperature increase due to absorbed radiation within the skin is a product of the local absorption coefficient and a local fluence divided by the volumetric specific heat. Since absorption and volumetric specific heat can be considered approximately constant within a region of skin, the local temperature rise can be considered proportional to the fluence.

Thermal damage to skin forms at temperatures at, or exceeding, a critical temperature ($T_c$). Little or no thermal damage to skin forms at temperatures below $T_c$. Therefore, depth of thermal damage to skin is approximately equal to the depth of skin that is exposed to a temperature of, or exceeding, $T_c$.

Figure 4A:
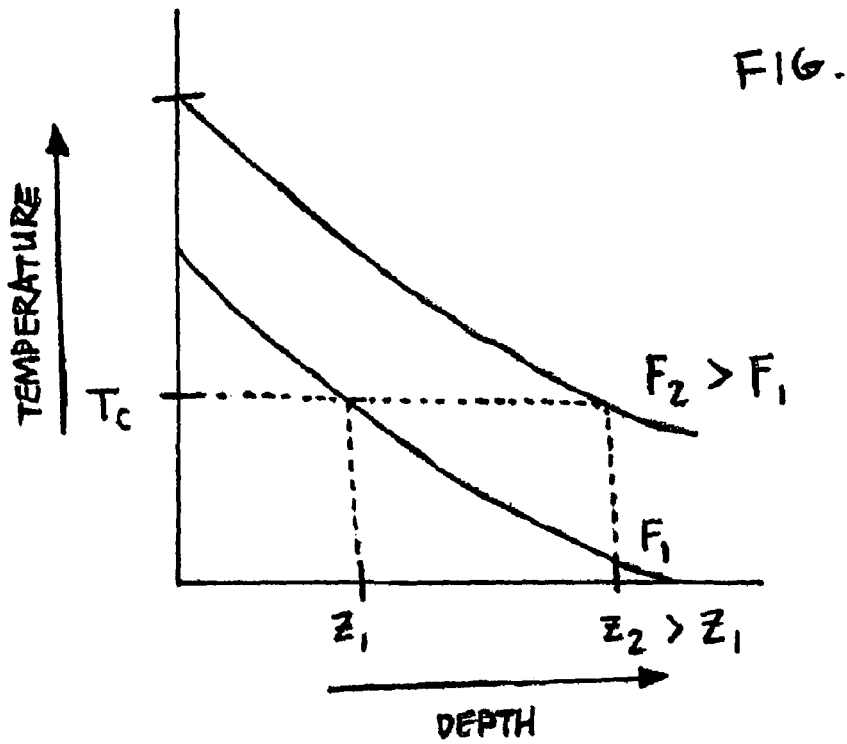
FIGS. 4A-4B show a relationship that can be used to control the temperature and thermal injury at a depth of a region of skin.

FIG. 4A shows a relationship that can be used to control the temperature at a depth of a region of skin. For a given temperature (T), a greater fluence can be selected if heating to a greater depth is desired and a lesser fluence can be selected if heating to a lesser depth is desired. This relationship can provide a method to control the depth to which a specific temperature is achieved.

Figure 4B:
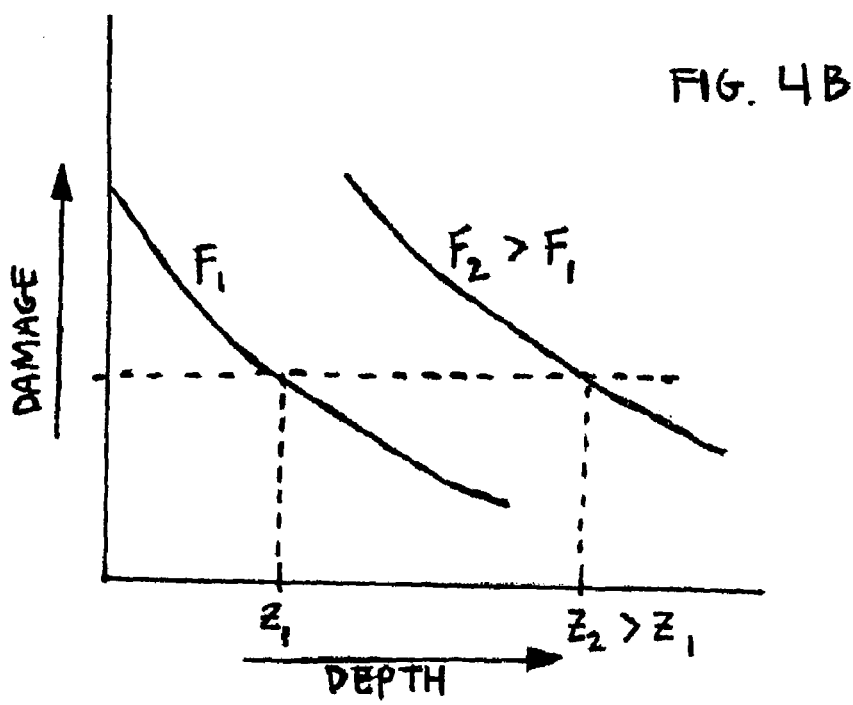

FIG. 4B shows a relationship that can be used to control a depth of thermal injury to a region of skin. A lower fluence produces a smaller depth of thermal injury and a higher fluence produces a greater depth of thermal injury. For a given degree of damage, a greater fluence can be selected if a greater depth is desired and a lesser fluence can be selected if a lesser depth is desired. Therefore, by modulating the fluence, one can modulate the depth and temperature within a region of skin.

To form deeper sub-zones of thermal injury, more penetrating wavelengths of radiation can be used. More penetrating wavelengths can be combined with longer pulse durations to increase thermal damage. In certain embodiments, more penetrating wavelengths can be combined with surface cooling to spare overlying tissue.

To form shallower sub-zones of thermal injury, less penetrating wavelengths can be used. Less penetrating wavelengths can be combined with shorter pulse durations. Less penetrating wavelengths can be used without surface cooling or with moderate cooling. Less penetrating wavelengths can also be used with surface cooling to maintain a temperature about a $T_c$ (e.g., allow formation of thermal injury, but prevent necrosis or acute thermal injury).

In various embodiments a beam of radiation with spatially varying intensity; a beam of radiation with spatially varying exposure time or pulse duration; a beam of radiation with spatially varying wavelengths wherein certain regions of the beam include a more penetrating wavelength and other parts include a less penetrating wavelength; and/or a beam of radiation with spatially varying wavelengths with preferential absorption in different skin structures (e.g., a beam including wavelengths with strong water absorption interspersed with wavelengths with strong blood absorption) can be delivered to a target region of the skin to cause a zone of thermal injury including a lateral pattern of varying depths.

In various embodiments, a pulse duration can be between about 1 ms and about 1 min. Shorter pulse durations can be between about 1 ms and about 100 ms. Longer pulse durations can be between about 100 ms and about 1 min.

In various embodiments, a depth of thermal injury in a deeper sub-zone can be up to about 2 mm. In certain embodiments, a depth of thermal injury in a shallower sub-zone can be up to about 50 µm. In one embodiment, deeper sub-zones having a depth of about 400-800 µm are adjacent to shallower sub-zones having a depth of about 50 µm. In another embodiment, deeper sub-zones having a depth of about 400-800 µm are adjacent to shallower sub-zones having a depth of about 25 µm. In still another embodiment, deeper sub-zones having a depth of about 1.5 mm are adjacent to shallower sub-zones having a depth of about 50 µm In various embodiments, adjacent sub-zones of thermal damage distributed contiguously along the surface of the target region can correspond to about 100% coverage of the surface of the target region (e.g., a substantially continuous surface injury). In certain embodiments, adjacent sub-zones of thermal damage distributed contiguously along the surface of the target region can correspond to less than 100% coverage of the surface of the target region.

In various embodiments, the target region includes about 0.5% to about 99% sub-zones of greater depth. In one embodiment, the target region includes about 5% to about 50% sub-zones of greater depth. In one embodiment, the target region includes about 15% to about 30% sub-zones of greater depth.

In various embodiments, a diameter of a deeper sub-zone of thermal damage can be between about 20 µm and about 2 mm. In some embodiments, a diameter of a shallower sub-zone of thermal damage can be between about 100 µm and about 1000 µm. In various embodiments, spacing between deeper sub-zones can be between about 2 to about 5 times the diameter of the deeper sub-zone. In various embodiments, spacing between shallower sub-zones is the sum of the diameters of the deeper and the shallower sub-zones. In certain embodiments, a sub-zone of thermal damage can have an aspect ratio of diameter:depth greater than 1:2. In one embodiment, a sub-zone of thermal damage has an aspect ratio greater than 1:4. In another embodiment, a sub-zone of thermal damage can have an aspect ratio up to about 0.1:10.

Figure 5A:
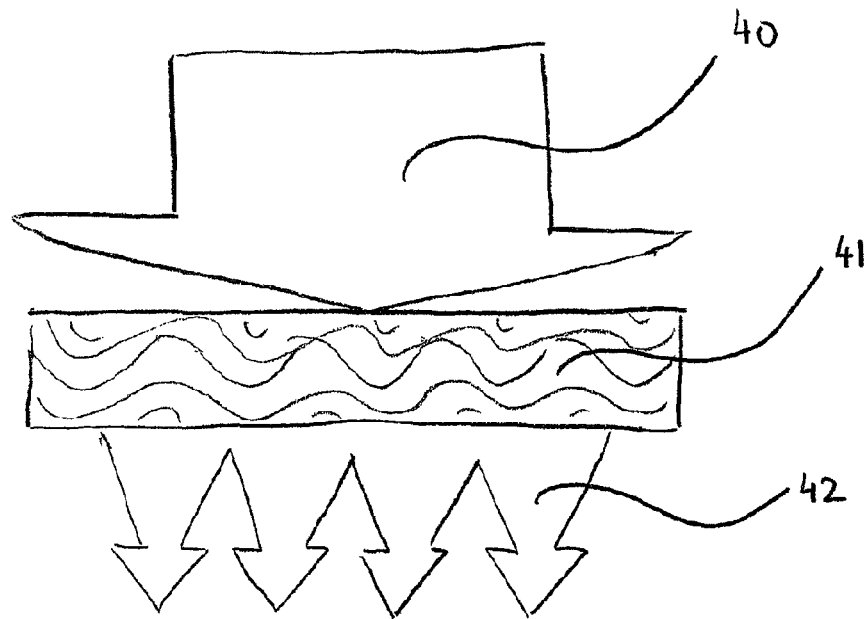
FIGS. 5A-5B shows examples of spatial modulation of a beam of radiation.

FIG. 5A shows an example of spatial modulation of a beam of radiation. A single 40 beam of radiation is incident on a modulator 41, which forms a spatially modulated 42 beam of radiation 42. In various embodiments, the modulator 41 can be an optical device and/or an electromagnetic device. For example, the modulator 41 can be a lens, a micro lens array, a system of lenses, a diffractive optic in combination with a lens, or another optical device capable of varying the fluence of the beam of radiation 40. In certain embodiments, the modulator is an acousto-optic modulator. In certain embodiments, the single 40 beam can be modulated to form a plurality of discrete beams.

Figure 5B:
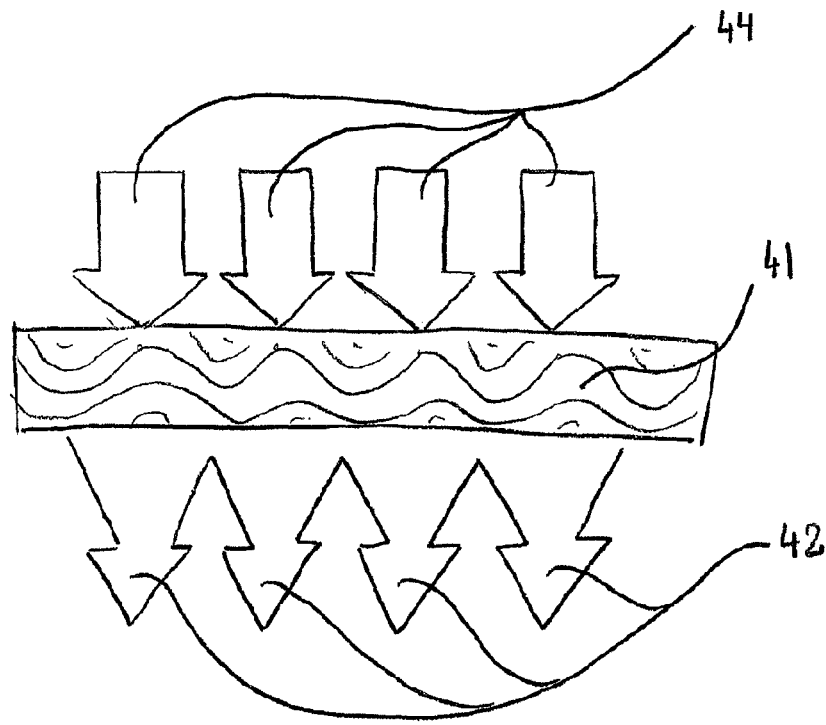

FIG. 5B shows another example of spatial modulation of a beam of radiation. A plurality 44 of beams of radiation are incident on a modulator 41, which forms the spatially modulated 42 beam of radiation. Regions of the discrete beams can overlap to form the spatially modulated beam of radiation 42.

In various embodiments, an optical fiber can be scanned over a surface of skin to deliver a spatially modulated beam of radiation to a target region of skin. In various embodiments, an optical fiber bundle can be used to deliver a plurality of beams of radiation. In certain embodiments, the optical fiber bundle can operate in a scanning mode over a surface of skin. In certain embodiments, the optical fiber bundle can operate in a stamping mode over a surface of skin. The diameter of a region of a surface of skin treated in each stamp can range from about 1 mm to about 50 mm. An optical fiber can be a fiber laser.

Figure 6:
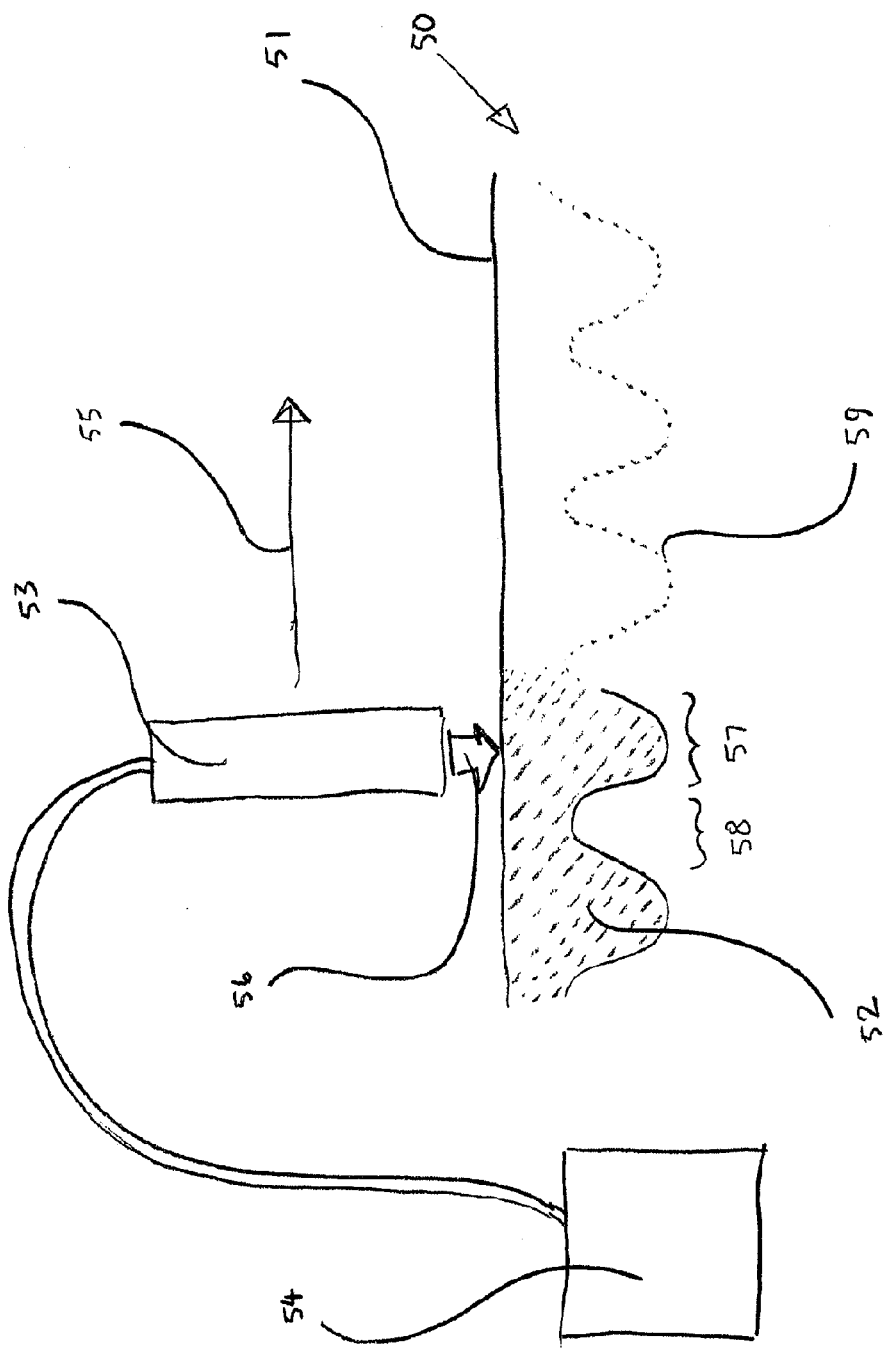
FIG. 6 shows an exemplary embodiment of a device for treating a region of skin.

FIG. 6 shows an exemplary embodiment of a device for treating a region of skin. A cross-section of skin 50 includes a skin surface 51 and a region 52 of thermal injury underlying the surface 51. A source 53 of a beam of radiation is coupled to a modulator 54. The source 53 can scan 55 along to the skin surface 51, to deliver a beam of radiation 56 to a target region of skin. The modulator 54 can modulate the fluence, the intensity, or the wavelength of the beam 56 and/or the rate of translation of the source 53.

By varying the fluence, the intensity, or the wavelength of the beam 56, the depth of injury can be controlled. Increasing the intensity of the beam 56 delivered to skin 50 can form a deeper zone of injury, e.g., a first sub-zone 57. Decreasing the intensity of the beam 56 delivered to skin 50 can form a shallow zone of injury, e.g., a second sub-zone 58. Varying the fluence or the intensity of the beam 56 can form a modulated spatial pattern 59 of thermal injury in skin.

By varying the rate of translation along the skin, the depth of thermal injury can be controlled. Decreasing the rate over skin 50 can increase the total fluence delivered to a particular region, forming a deeper zone of injury, e.g., a first sub-zone 57. Increasing the rate over skin 50 can decrease the total fluence delivered to a particular region, forming a shallow zone of injury, e.g., a second sub-zone 57. Varying the rate of translation along the skin, can form a modulated spatial pattern 59 of thermal injury in skin.

In some embodiments, methods can include sequentially applying different combinations of radiation wavelength, intensity, or cooling such that a pattern of thermal injury achieved in a given pass is different than that achieved in a subsequent pass.

A cooling system can be used to modulate the temperature in a region of skin and/or minimize unwanted thermal injury to untargeted skin. For example, the delivery system 13 shown in FIG. 2 can be used to cool the skin before, during, or after delivery of radiation, or a combination of the aforementioned. Cooling can include contact conduction cooling, evaporative spray cooling, convective air flow cooling, or a combination of the aforementioned. Cooling can include applying a template to the skin and employing contact, evaporative, or convective cooling to cool at least an exposed portion of the skin. In one embodiment, the handpiece 16 includes a skin contacting portion that can be brought into contact with a region of skin. The skin contacting portion can include a sapphire or glass window and a fluid passage containing a cooling fluid. The cooling fluid can be a fluorocarbon type cooling fluid, which can be transparent to the radiation used. The cooling fluid can circulate through the fluid passage and past the window to cool the skin.

A spray cooling device can use cryogen, water, or air as a coolant. In one embodiment, a dynamic cooling device (e.g., a DCD available from Candela Corporation) can be used to cool the skin. For example, the delivery system 13 shown in FIG. 2 can include tubing for delivering a cooling fluid to the handpiece 16. The tubing can be connected to a container of a low boiling point fluid, and the handpiece can include a valve for delivering a spurt of the fluid to the skin. Heat can be extracted from the skin by virtue of evaporative cooling of the low boiling point fluid. In one embodiment, the fluid is a non-toxic substance with high vapor pressure at normal body temperature, such as a Freon or tetrafluoroethane.

By cooling only a portion of the target region or by cooling different portions of the target region to different extents, the degree of thermal injury of individual portions of the target region can be controlled. By cooling with spatially varying duration and/or by cooling with spatially varying temperature, the degree of thermal injury of individual portions of the target region can also be controlled.

Figure 7A:
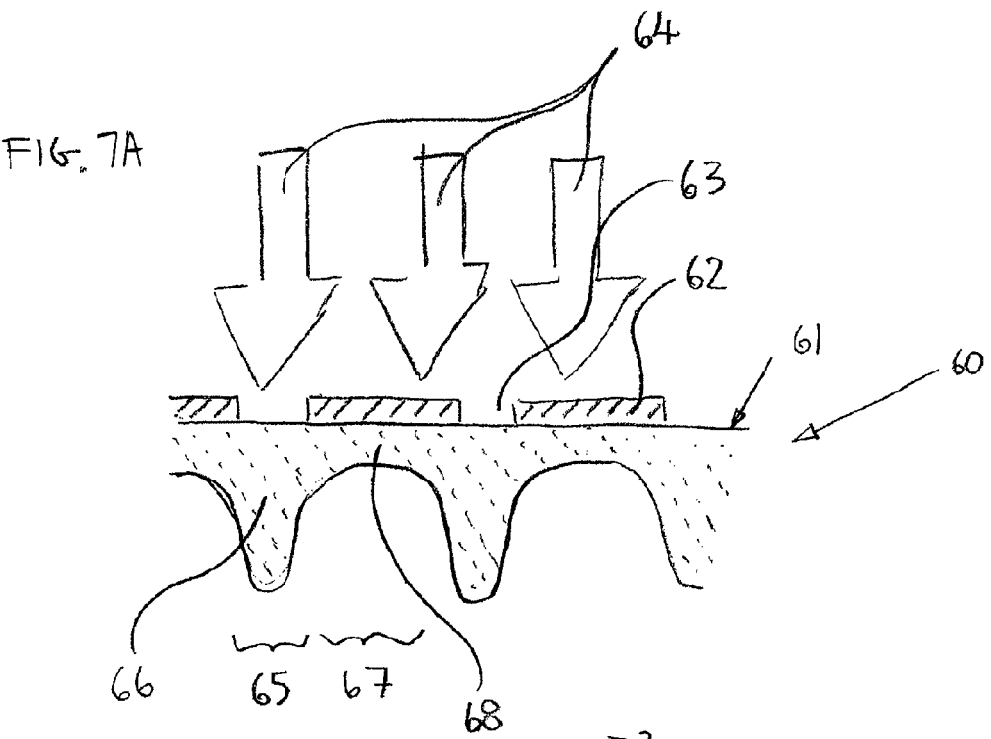
FIGS. 7A-7C show exemplary treatments of skin using cooling.

FIG. 7A shows an exemplary treatment of skin using cooling. A cross-section of a region of skin 60 includes a skin surface 61. A cooling plate 62 is applied to the skin surface 61, and a region 63 of skin not in contact with the cooling plate 62 is formed. A beam of radiation 64 is delivered to the region of skin 60, to treat the skin.

The cooling plate 62 can be applied to the skin surface 61 prior to or during delivery of the beam of radiation 64. In some embodiments, the cooling plate 62 can have at least one open region, corresponding to the region 63 of skin not in contact with the cooling plate 62.

The cooling plate 62 can cool different regions of the target region to different extents thus modulating a spatial profile of temperature in the skin 60. For example, skin underlying the region 63 not in contact with the cooling plate 62 can be cooled to a first temperature, and skin underlying the cooling plate 62 can be cooled to a second temperature. The first temperature is greater than the second temperature.

In some embodiments, the cooling plate 62 can be continuous (e.g., not have open regions), but have regions of varying thickness. Thicker regions of the cooling plate can extract more heat from the skin than thinner regions, thus a deeper zone of thermal injury can be formed under the thinner regions.

In FIG. 7A skin region 66 represents a deeper zone of thermal injury. Skin region 68 represents a shallower zone of thermal injury, e.g., where the skin 60 is substantially undamaged.

Figure 7B:
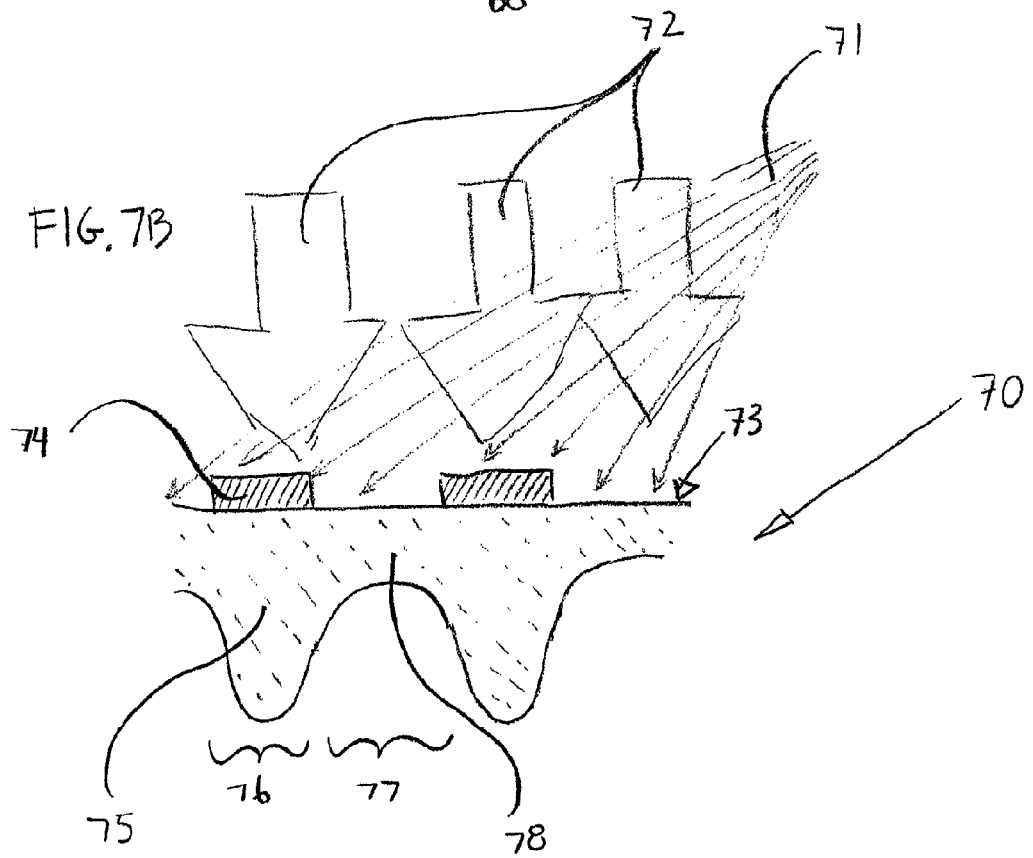

FIG. 7B shows another exemplary treatment of skin using cooling. A cross-section of a treatment region of skin 70 is treated with a cryogen spray 71 and a beam 72 of radiation. At least a region of the skin surface 73 is in contact with a laser-transparent spray screen 74, which can be applied to the skin surface 73 prior to delivery of the cryogen spray 71. The cryogen spray 71 can be applied prior to or during delivery of the beam 72 of radiation to cool different regions of the target region to different extents.

The screen 74 can modulate a spatial profile of temperature in skin by preventing the cryogen spray 71 from reaching at least a region of the surface 73. In certain embodiments, the screen 74 is not used and the cryogen spray 71 is applied to the skin surface 73 in pools of varying depth. A deeper pool can extract more heat from the skin surface 73, thus forming a region of shallow injury when radiation is delivered.

In FIG. 7B the beam 72 of radiation is delivered to the surface 73 of skin with at least one underlying region 76 of skin of first temperature and at least one underlying region 77 of skin of second temperature. The first temperature is greater than the second temperature. Delivery of the beam 72 of radiation can increase the temperature in the target region. In a region 76 of skin of first temperature, delivery of the beam 72 of radiation can increase the temperature above a critical temperature, forming a first sub-zone 75 of thermal injury. In a region 77 of skin of second temperature, delivery of the beam of radiation can increase the temperature to a second temperature below the first temperature. In some embodiments, the region 77 of skin of second temperature can remain substantially undamaged. In some embodiments, the region 77 of skin of second temperature can form a second sub-zone 78 of thermal injury.

Figure 7C:
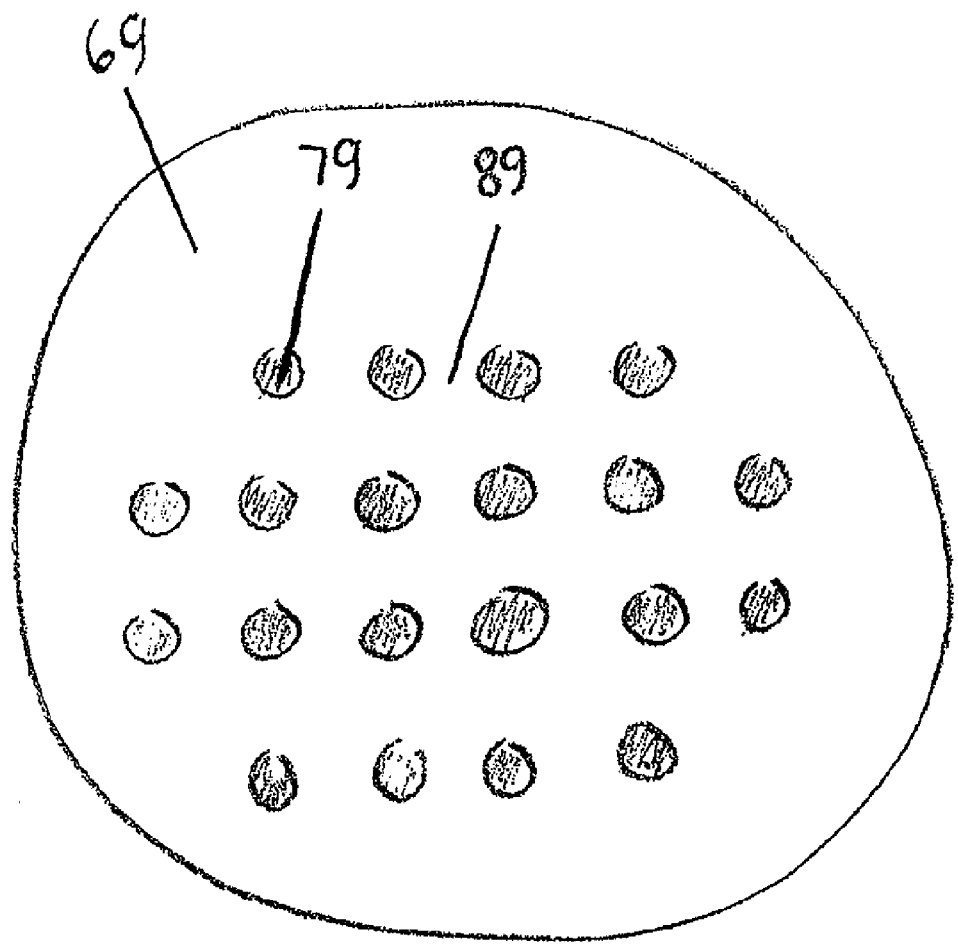

FIG. 7C shows yet another exemplary treatment of skin using cooling, specifically a skin surface 69 with at least one first 79 region and at least one second 89 region. The at least one first 79 region and at least one second 89 region can form a regular or irregular array. In one treatment, the target region can be cooled to produce at least one first 79 region at a first temperature and at least one second 89 region at a second temperature, the first temperature being greater than the second temperature. The at least one first 79 region can correspond to the at least one first sub-zone, and the at least one second 89 region corresponding to the at least one second sub-zone. In another example, the method can include cooling the target region of skin to produce at least one first 79 region cooled to a first depth and at least one second 89 region cooled to a second depth, the first depth being less than the second depth. The at least one first 79 region can correspond to the at least one first sub-zone, and the at least one second 89 region corresponding to the at least one second sub-zone. In general, the depth and/or temperature within the target region can be controlled by the duration and/or temperature of the cooling. For example, a greater duration can cool to a greater depth and a lower temperature can cool to a lower temperature.

Sub-zones of thermal damage can form different geometries. In various embodiments, sub-zone geometries can include cylinders, cones, cuboids, spheroids, ellipsoids, and ovoids. Any of these sub-zone geometries can be overlaid with, or combined with, a substantially continuous surface thermal injury.

Figure 8A:
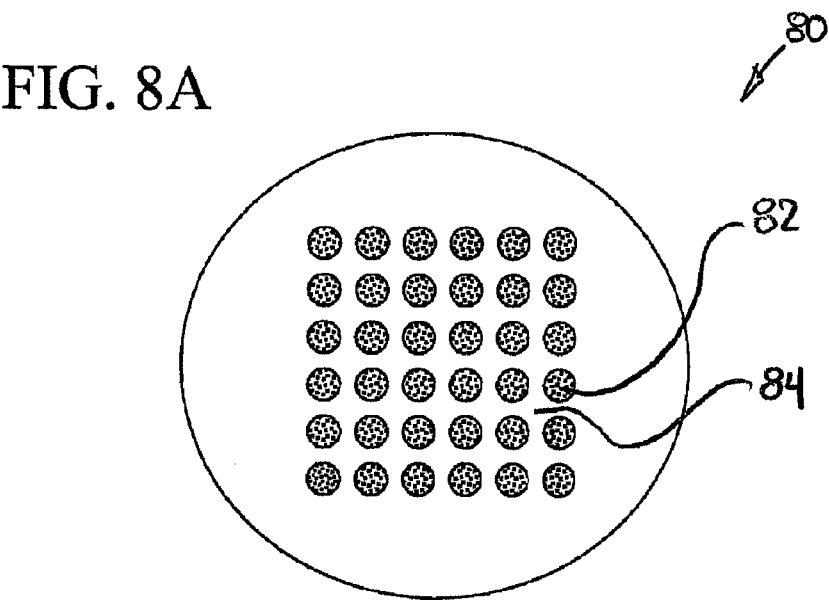
FIGS. 8A-8B show exemplary embodiments of a surface of a treated region of skin with a pattern of varying depths of thermal injury.

FIG. 8A shows an exemplary embodiment of a surface 80 of a treated region of skin with a pattern of varying depths of thermal injury. A regular two-dimensional array of a plurality of sub-zones of a first depth 82 of thermal injury are adjacent to a plurality of sub-zone of a second depth 84 of thermal injury.

In another embodiment, a plurality of sub-zones of a first depth of thermal injury adjacent to a plurality of sub-zones of a second depth of thermal injury can form a one-dimensional array (e.g., a curvilinear pattern). Such a pattern can, for example, trace the contour of a wrinkle, vein, scar, or skin defect. In certain embodiments, methods can include varying a pattern over different parts of the skin to achieve different desired effects (e.g., to produce a pattern of surface injury in an area with surface wrinkles, while producing a pattern of sub-surface injury in an area for skin tightening with less surface injury).

Figure 8B:
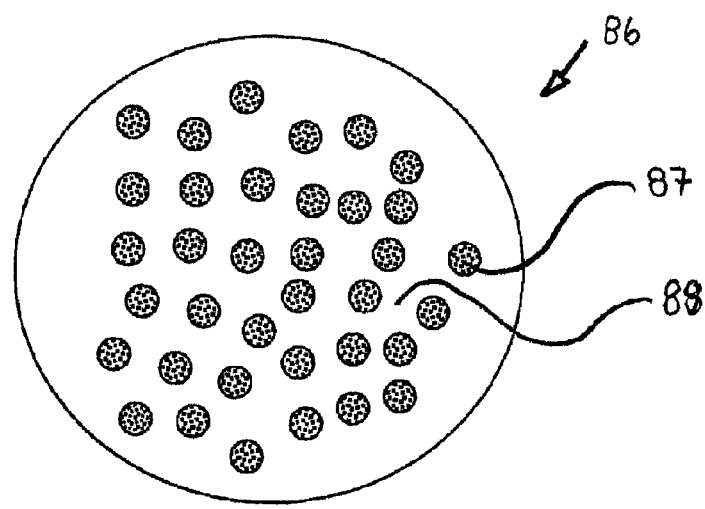

FIG. 8B shows an exemplary embodiment of a surface 86 of a treated region of skin with a pattern of varying depths of thermal injury. An irregular array of a plurality of sub-zones of a first depth 87 of thermal injury are adjacent to a plurality of sub-zone of a second depth 88 of thermal injury.

Figure 9:
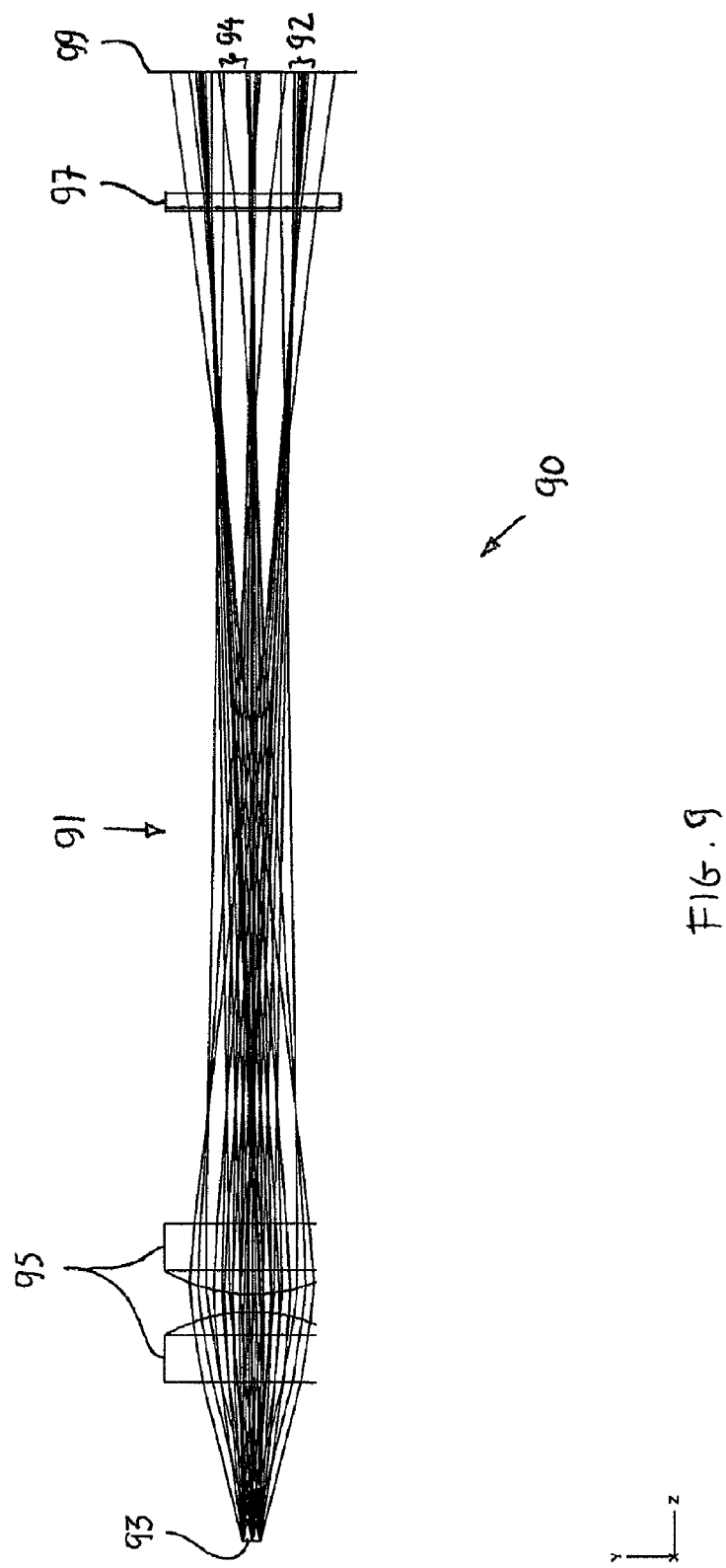
FIG. 9 shows a ray trace of modulated electromagnetic radiation.

FIG. 9 shows a ray trace 90 of modulated electromagnetic radiation. The electromagnetic radiation is represented by a plurality of rays 91, which are emitted from a fiber face 93. The rays 91 are imaged by two lenses 95 and then spatially modulated by a micro lens 97 array before delivery to the skin 99 surface. A first region 92 of the skin surface, upon which more rays 91 are incident, can correspond to a first sub-zone of a first depth of thermal injury. A second region 94 of the skin surface, upon which fewer rays 91 are incident, can correspond to a second sub-zone of a second depth of thermal injury.

Figure 10:
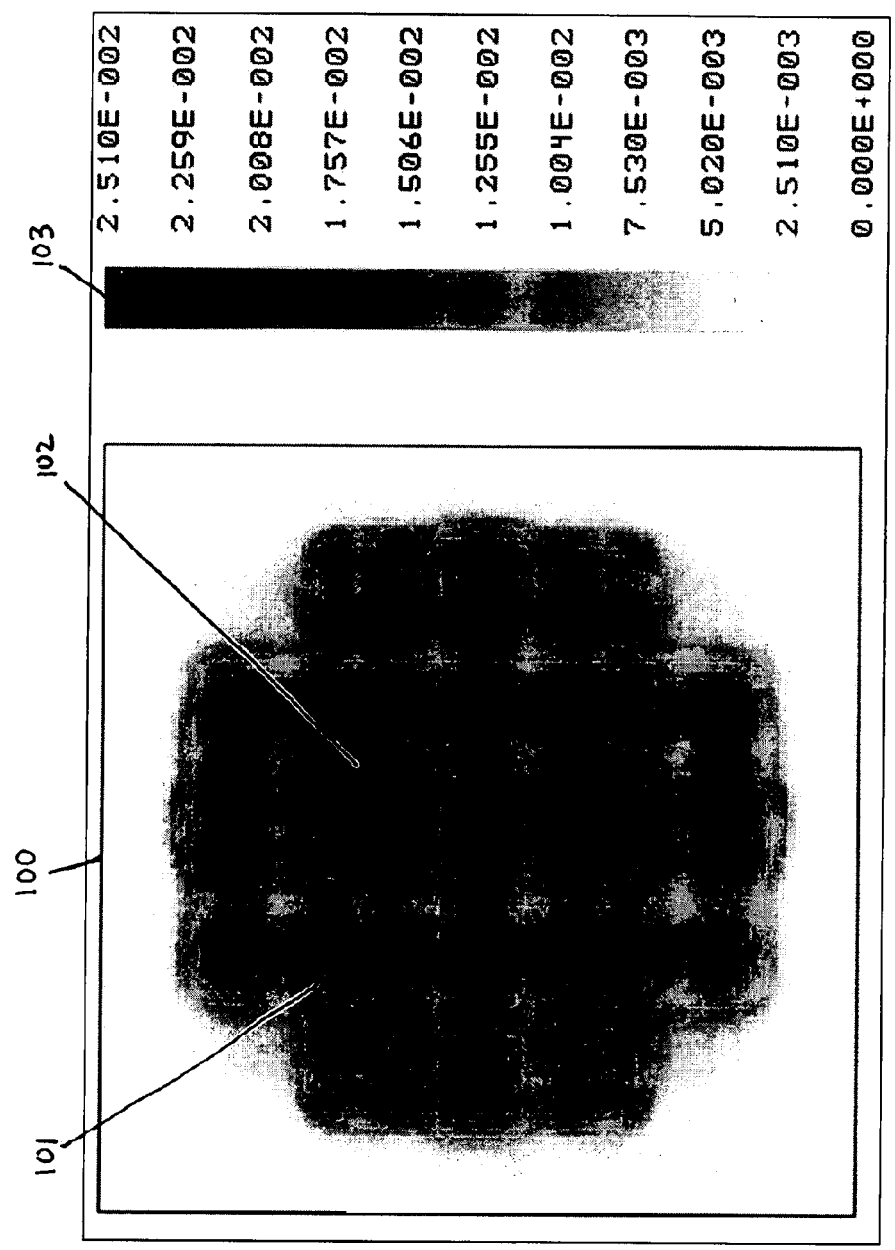
FIG. 10 shows a contour plot of energy density on skin created by modulated electromagnetic radiation.

FIG. 10 shows a contour plot 100 of energy density on skin created by modulated electromagnetic radiation. A position of high 101 energy density can correspond to a first sub-zone of a first depth of thermal injury and a position of low 102 energy density can correspond to a second sub-zone of a second depth of thermal injury. The legend 103 of the contour plot 100 shows the energy density in units of W/mm$^2$. The contour plot 100 represents an area of about 7 mm by about 7 mm.

Figure 11:
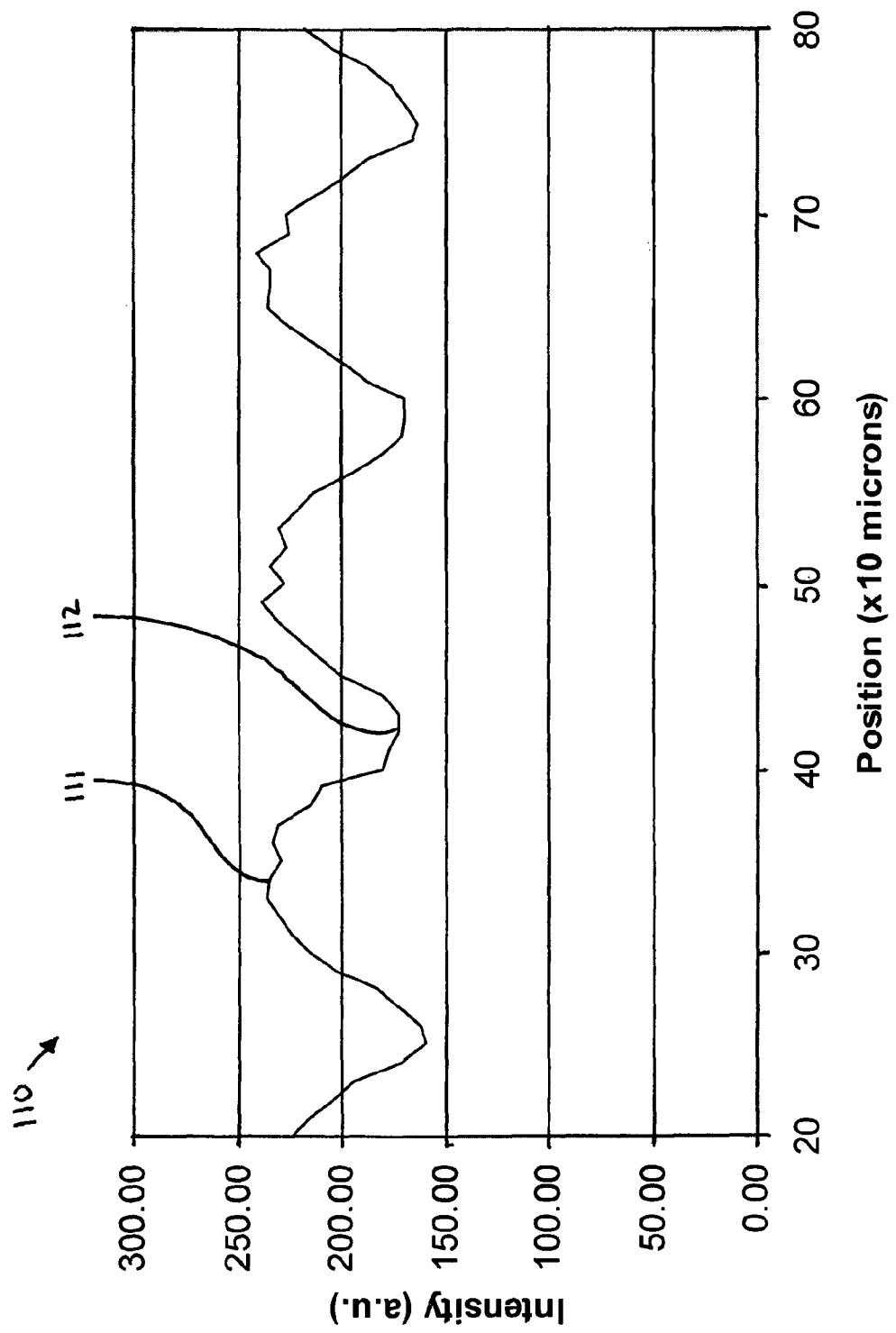
FIG. 11 shows a plot of intensity variation across skin created by modulated electromagnetic radiation.

FIG. 11 shows a plot 110 of intensity variation across skin created by modulated electromagnetic radiation. The y-axis shows the intensity of energy in arbitrary units (a.u.) and the x-axis shows the position in microns. A position of high 111 energy density can correspond to a first sub-zone of a first depth of thermal injury and a position of low 112 energy density can correspond to a second sub-zone of a second depth of thermal injury.

While the invention has been particularly shown and described with reference to specific embodiments, it should be understood by those skilled in the art that various changes in form and detail may be made therein without departing from the spirit and scope of the invention as defined by the appended claims.

What is claimed is:

1. An apparatus for treating skin comprising:
   a source of a beam of radiation;
   a modulator receiving the beam of radiation and forming a modulated spatial profile of the beam including a first plurality of first regions at a first fluence and a second plurality of second regions at a second fluence, the first fluence being greater than the second fluence, each first region being spaced from an adjacent first region by a respective second region; and
   a device for delivering the beam of radiation to a target region of skin to cause a zone of thermal injury including a lateral pattern of varying depths of thermal injury distributed along the target region, the lateral pattern including at least one first sub-zone of a first depth of thermal injury laterally adjacent to at least one second sub-zone of a second depth of thermal injury, wherein (i) the first depth is greater than the second depth, (ii) the at least one first sub-zone of the first depth and the at least one second sub-zone of the second depth extend from a surface of the target region of the skin to form a substantially continuous surface thermal injury, and (iii) the at least one first sub-zone of the first depth and the at least one second sub-zone of the second depth are substantially heated to at least a critical temperature to cause the thermal injury.

2. The apparatus of claim 1 further comprising a cooling system for controllably cooling at least a portion of the target region of skin, to control the thermal injury within the target region.

3. The apparatus of claim 1 further comprising a cooling system for cooling the target region of skin to produce at least one first region at a first temperature and at least one second region at a second temperature, the first temperature being greater than the second temperature, the at least one first region corresponding to the at least one first sub-zone, and the at least one second region corresponding to the at least one second sub-zone.

4. The apparatus of claim 1 further comprising a cooling system for cooling the target region of skin to produce at least one first region cooled to a first depth and at least one second region cooled to a second depth, the first depth being less than the second depth, the at least one first region corresponding to the at least one first sub-zone, and the at least one second region corresponding to the at least one second sub-zone.

5. The apparatus of claim 1, wherein the source of a beam of radiation provides a beam of radiation with spatially varying intensity; with spatially varying exposure time or pulse duration and with spatially varying wavelengths.

6. The apparatus according to claim 1, wherein certain regions of the beam of radiation include a more skin penetrating wavelength and other regions of the beam of radiation include a less skin penetrating wavelength.

7. The apparatus according to claim 1, wherein the beam of radiation includes spatially varying wavelengths with strong water absorption interspersed with wavelengths with strong blood absorption and wherein the beam of radiation when delivered to a target region of the skin is configured to cause a zone of thermal injury including a lateral pattern of varying depths.

8. The apparatus according to claim 1, wherein the modulator delivers the beam of radiation to a target region of the skin to form a two-dimensional lateral pattern of varying depths of thermal injury and wherein the two-dimensional lateral pattern includes a plurality of sub-zones of a first depth of thermal injury adjacent to a plurality of sub-zone of a second depth of thermal injury.

9. The apparatus according to claim 1, wherein the apparatus includes at least one of a group of energy sources consisting of an incoherent light source, a coherent light source, a solid state laser, a diode laser, a fiber coupled diode laser array, an optically combined diode laser array, and/or a high power semiconductor laser.

10. The apparatus according to claim 9, wherein at least two energy sources are used together to effect a skin treatment and wherein one of the energy sources is an incoherent source to provide a first beam of radiation and a coherent source to provide a second beam of radiation.

11. The apparatus according to claim 1, wherein the modulator, which forms a spatially modulated beam of radiation is one of a group consisting of a lens, a micro lens array, a system of lenses, a diffractive optic in combination with a lens, an acousto-optic modulator and an optical device capable of varying the fluence of the beam of radiation.

12. The apparatus according to claim 1, wherein the modulator modulates a single beam to form a plurality of discrete beams.

13. The apparatus according to claim 1, further comprising:
- an energy source configured to provide the beam of radiation;
- a delivery system configured to deliver the beam of radiation to a target area of the skin,
- wherein the delivery system includes a fiber with a circular cross-section; and
- a handpiece including an optical system to direct the beam of radiation to the target area of the skin.

14. The apparatus according to claim 13, wherein the handpiece includes a spacer to space the delivery system from the skin.

* * * * *